United States Patent
Harris et al.

(10) Patent No.: US 8,685,401 B2
(45) Date of Patent: Apr. 1, 2014

(54) METHODS OF ENHANCING THE RESPONSE TO RADIATION IN TUMOR THERAPY USING ANTI-DLL4 ANTIBODIES

(76) Inventors: Adrian Harris, Oxford (GB); Stanley Liu, Tornoto (CA); Ruth Muschel, Oxford (GB)

( * ) Notice: Subject to any disclaimer, the term of this patent is extended or adjusted under 35 U.S.C. 154(b) by 0 days.

(21) Appl. No.: 13/524,396

(22) Filed: Jun. 15, 2012

(65) Prior Publication Data
US 2013/0006034 A1    Jan. 3, 2013

Related U.S. Application Data

(60) Provisional application No. 61/498,220, filed on Jun. 17, 2011.

(51) Int. Cl.
*A61K 39/395*    (2006.01)

(52) U.S. Cl.
USPC .................................... 424/145.1; 530/387.1

(58) Field of Classification Search
None
See application file for complete search history.

(56) References Cited

U.S. PATENT DOCUMENTS 7,750,124 B2 *    7/2010    Gurney et al. ............. 530/387.3
2011/0059114 A1    3/2011    Sullenger et al.

FOREIGN PATENT DOCUMENTS

WO    WO 2008/042236    4/2008
WO    WO 2010/032060    3/2010

OTHER PUBLICATIONS

Rakesh K. Jain, Barriers to Drug Delivery in Solid Tumors, 1994, Scientific Journal, pp. 58-65.*
Michael B. Sporn, Chemoprevention of cancer,2000, Carcinogenesis, vol. 21 No. 3, pp. 535-530.*
Trisha Gura, Systems for Identifying New Drugs are Often Faulty, 1997, Science, vol. 278 No. 5340, pp. 1041-1042.*
Robert Auerbach, Angiogenesis assays: Problems and Pitfalls, 2000, Cancer and Metastasis Reviews, vol. 19, pp. 167-17.*
Stephen Neidle, Cancer Drug Design and Discovery, 2008, Elsevier/Academic Press, pp. 427-431.*
Phase I/II Trial of Bevacizumab and Radiotherapy for Locally Advanced Inoperable Colorectal Cancer: Vasculature-Independent Radiosensitizing Effect of Bevacizumab Michael I. Koukourakis, et al.Clin Cancer Res Nov. 15, 2009 15:22 7069-7076.*
Hovinga et al., "Inhibition of Notch Signaling in Glioblastoma Targets Cancer Stem Cells via an Endothelial Cell Intermediate," *Stem Cells*, vol. 28, 2010, www.StemCells.com, pp. 1019-1029.
Liu et al., "Delta-Like Ligand 4-Notch Blockade and Tumor Radiation Response," *JNCI*, vol. 108, Issue 23, Dec. 7, 2011, pp. 1778-1798.
Wang et al., "Notch Promotes Radioresistance of Glioma Stem Cells," *Stem Cells*, vol. 28, 2010, www.StemCells.com, pp. 17-28.
PCT International Search Report and Written Opinion for International Patent Application No. PCT/US2012/042695, dated Oct. 4, 2012 (13 pages).

* cited by examiner

*Primary Examiner* — Brian J Gangle
*Assistant Examiner* — Andrea McCollum
(74) *Attorney, Agent, or Firm* — Finnegan, Henderson, Farabow, Garrett & Dunner, LLP

(57) ABSTRACT

The disclosure provides methods of treating cancer, tumors, and neoplasias by administering ionizing radiation and an anti-DLL4 antibody or a DLL4-binding fragment.

17 Claims, 22 Drawing Sheets

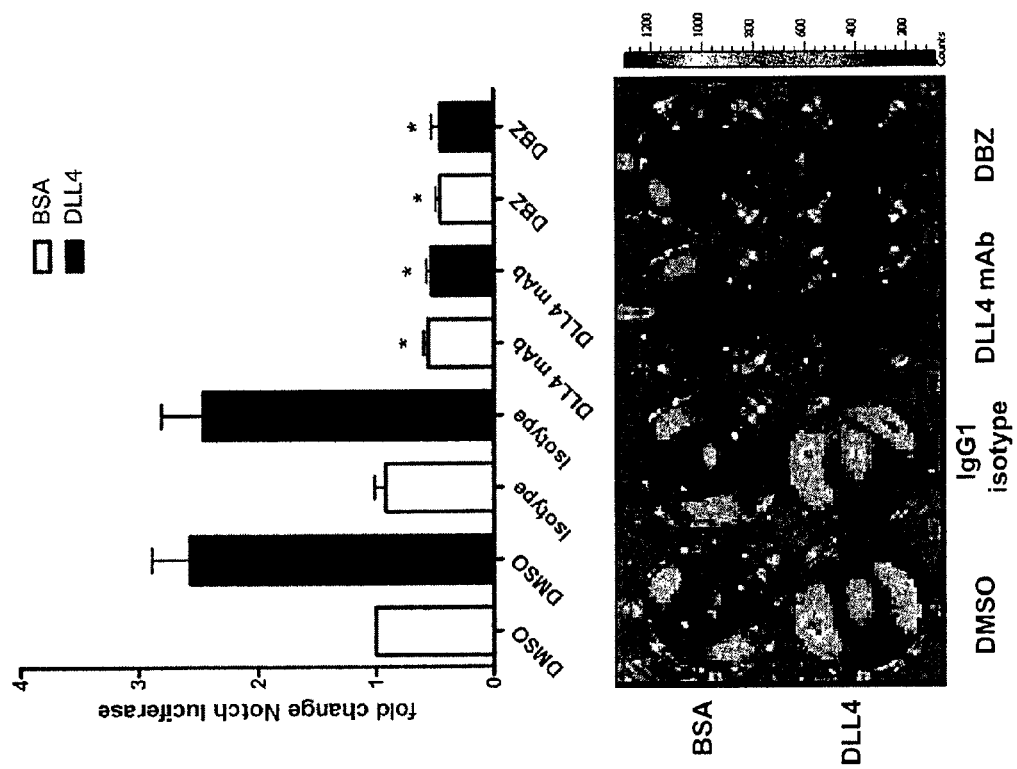

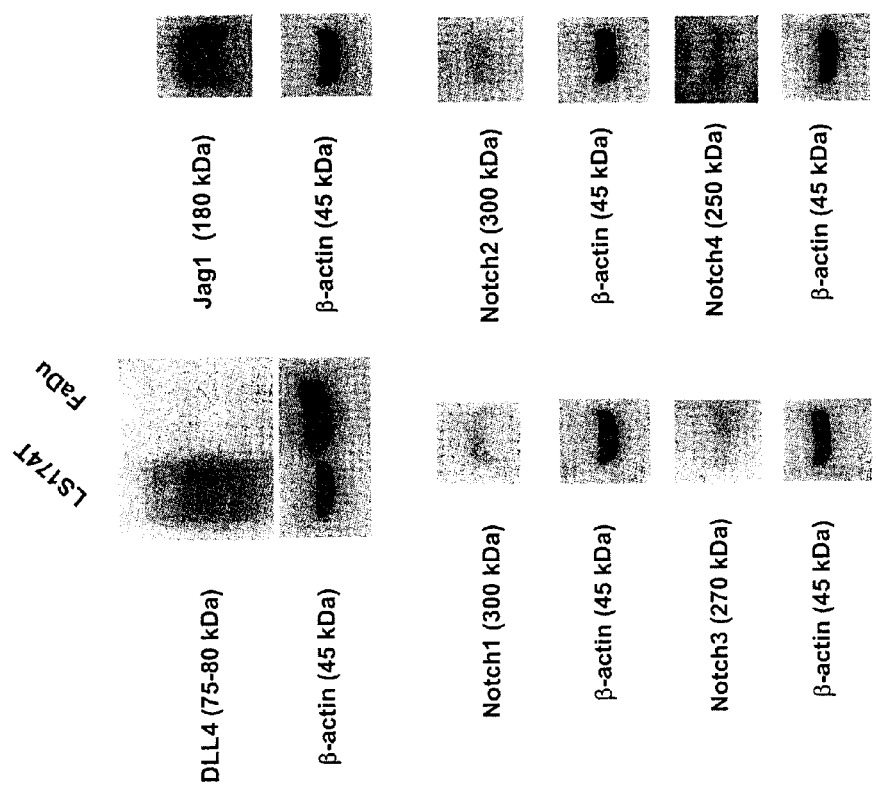

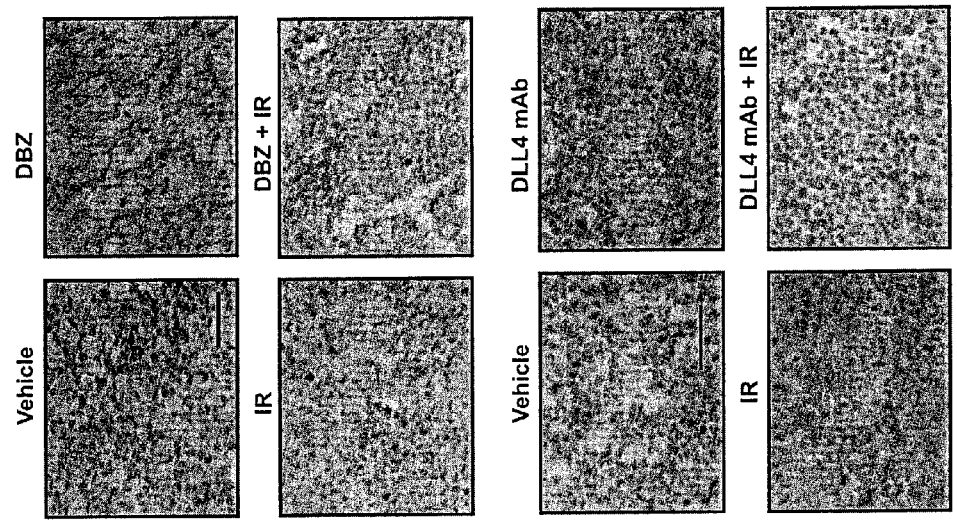

SEQUENCE LISTING

<160> NUMBER OF SEQ ID NOS: 8

<210> SEQ ID NO 1
<211> LENGTH: 5
<212> TYPE: PRT

```
<213> ORGANISM: Unknown
<220> FEATURE:
<223> OTHER INFORMATION: First complementarity-determining region (CDR1)
      of a heavy chain variable domain of an anti-DLL4 (Delta-like
      Ligand 4) binding fragment

<400> SEQUENCE: 1

Asn Tyr Gly Ile Thr
1               5

<210> SEQ ID NO 2
<211> LENGTH: 17
<212> TYPE: PRT
<213> ORGANISM: Unknown
<220> FEATURE:
<223> OTHER INFORMATION: Second complementarity-determining region
      (CDR2) of a heavy chain variable domain of an anti-DLL4 (Delta-
      like Ligand 4) binding fragment

<400> SEQUENCE: 2

Trp Ile Ser Ala Tyr Asn Gly Asn Thr Asn Tyr Ala Gln Lys Leu Gln
1               5                   10                  15

Asp

<210> SEQ ID NO 3
<211> LENGTH: 15
<212> TYPE: PRT
<213> ORGANISM: Unknown
<220> FEATURE:
<223> OTHER INFORMATION: Third complementarity-determining region (CDR3)
      of a heavy chain variable domain of an anti-DLL4 (Delta-like
      Ligand 4) binding fragment

<400> SEQUENCE: 3

Asp Arg Val Pro Arg Ile Pro Val Thr Thr Glu Ala Phe Asp Ile
1               5                   10                  15

<210> SEQ ID NO 4
<211> LENGTH: 13
<212> TYPE: PRT
<213> ORGANISM: Unknown
<220> FEATURE:
<223> OTHER INFORMATION: First complementarity-determining region (CDR1)
      of a light chain variable domain of an anti-DLL4 (Delta-like
      Ligand 4) binding fragment

<400> SEQUENCE: 4

Ser Gly Ser Ser Ser Asn Ile Gly Ser Tyr Phe Val Tyr
1               5                   10

<210> SEQ ID NO 5
<211> LENGTH: 7
<212> TYPE: PRT
<213> ORGANISM: Unknown
<220> FEATURE:
<223> OTHER INFORMATION: Second complementarity-determining region
      (CDR2) of a light chain variable domain of an anti-DLL4
      (Delta-like Ligand 4) binding fragment

<400> SEQUENCE: 5

Arg Asn Asn Gln Arg Pro Ser
1               5

<210> SEQ ID NO 6
<211> LENGTH: 12
<212> TYPE: PRT
<213> ORGANISM: Unknown
<220> FEATURE:
<223> OTHER INFORMATION: Third complementarity-determining region (CDR3)
```

-continued of a light chain variable domain of an anti-DLL4 (Delta-like
         Ligand 4) binding fragment

<400> SEQUENCE: 6

Ala Ala Trp Asp Asp Ser Leu Ser Gly His Trp Val
 1               5                  10

<210> SEQ ID NO 7
<211> LENGTH: 60
<212> TYPE: PRT
<213> ORGANISM: Unknown
<220> FEATURE:
<223> OTHER INFORMATION: Heavy chain variable domain of an anti-DLL4
      (Delta-like Ligand 4) binding fragment

<400> SEQUENCE: 7

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Gly Ile Thr Trp Val Arg Gln Ala Pro Gly Gln Gly Pro Ala Phe Asp
        35                  40                  45

Ile Trp Gly Gln Gly Thr Met Val Thr Val Ser Ser
    50                  55                  60

<210> SEQ ID NO 8
<211> LENGTH: 111
<212> TYPE: PRT
<213> ORGANISM: Unknown
<220> FEATURE:
<223> OTHER INFORMATION: Light chain variable domain for an anti-DLL4
      (Delta-like Ligand 4) binding fragment

<400> SEQUENCE: 8

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Tyr
            20                  25                  30

Phe Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Glu Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly His Trp Val Phe Gly Gly Thr Lys Leu Thr Val Leu
                100                 105                 110

METHODS OF ENHANCING THE RESPONSE TO RADIATION IN TUMOR THERAPY USING ANTI-DLL4 ANTIBODIES

RELATED APPLICATIONS

The present application claims priority from U.S. Provisional Application No. 61/498,200, filed Jun. 17, 2011, the contents which are incorporated herein by reference.

FIELD OF THE INVENTION

The present invention relates to the field of cancer, tumor, and neoplasia treatment using an anti-DLL4 antibody, or a DLL4-binding fragment, in combination with radiation therapy.

DESCRIPTION OF THE RELATED ART

Vascular endothelial growth factor (VEGF) is an important stimulatory factor for tumor angiogenesis. Targeting the VEGF pathway reduces tumor vessel density and slows tumor growth in preclinical mouse xenograft models. A humanized anti-VEGF monoclonal Ab (mAb), bevacizumab, has been incorporated into chemotherapeutic regimes for a variety of solid tumors with modest improvements in overall and progression-free survival (Ebos et al., Clin Cancer Res. 2009, 15(16):5020-5). However, resistance to VEGF blockade is common (Ebos et al., Clin Cancer Res. 2009, 15(16):5020-5; Bergers & Hanahan, Nat Rev Cancer 2008, 8(8):592-603; Kerbel R S., N Engl J Med. 2008, 358(19):2039-49). Recently this has been shown to be related to another pathway regulating angiogenesis—Delta-like ligand 4 (DLL4) or Notch signaling (Noguera-Troise et al., Nature 2006, 444(7122):1032-7; Ridgway et al., Nature 2006, 444(7122):1083-7; Benedito et al. Cell 2009, 137(6):1124-35; Li & Harris, Cancer Cell 2005, 8(1):1-3; Li et al., Cancer Res. 2007, 67(23):11244-53; Hoey, et al., Cell Stem Cell 2009, 5(2):168-77).

In mammals, there are four Notch receptors (Notch 1-4), and five Notch ligands (Jagged-1, -2, and Delta-like-1, -3, and -4). Ligand binding to the extracellular subunit of Notch triggers proteolytic cleavages by enzymes such as TNF-alpha converting enzyme (TACE) and gamma-secretase, which results in the creation of Notch intracellular domains (NICD) that translocate to the nucleus and bind to transcription factors, ultimately resulting in the activation of downstream target genes (Bray, Nat. Rev. Mol. Cell. Biol. 2006, 7:678). Emerging evidence suggests that multiple Notch pathway components are expressed in the vasculature and that aberrations in normal Notch signaling can result in vascular phenotypes. For example, mutations in Jagged 1 and Notch 3 result in Alagille syndrome and cerebral autosomal dominant arteriopathy with subcortical infarcts and leukoencephalopathy, respectively, two disorders that exhibit vascular defects. Furthermore, genetic deletion of Notch1 and DLL4 in mice all result in embryonic lethality with vascular abnormalities. In addition, deletion of a single allele of DLL4 in mice results in embryonic lethality with severe vascular defects in most genetic backgrounds (Duarte et al., Genes Dev. 2004, 18:2474; Gale et al., Proc. Nat. Acad. Sci. 2004, 101:15949). This phenotype has only previously been reported for VEGF-A and suggests that DLL4 may also play an important role in vascular development.

The Notch pathway is an important regulator of tumor angiogenesis, primarily through Notch ligands DLL4 and Jagged-1. It is upregulated in a wide range of human cancers including breast and colon carcinoma (Stylianou et al., Cancer Res. 2006, 66(3):1517-25; Callahan & Egan, J Mammary Gland Biol Neoplasia 2004, 9(2):145-63; Reedijk et al., Cancer Res. 2005, 65(18):8530-7; Reedijk et al., Int J Oncol. 2008, 33(6):1223-9; Sikandar et al., Cancer Res. 2010, 70(4):1469-78). In addition to effects on angiogenesis, Notch signaling has also been implicated in cancer stem cells ("CSC") from multiple tumor types (Dontu et al., Breast Can. Res. 2004, 6:R605; Wilson & Radtke, FEBS Lett. 2006, 580:2860). Cancer stem cells have been isolated from a variety of hematopoietic and solid tumors (Al-Hajj et al., Proc. Nat. Acad. Sci. 2003, 100:3983; Lapidot et al., Nature 1994, 17:645; Tan et al., Laboratory Investigation 2006, 86:1203) and the presence of DLL4 on small populations of tumor cells further suggests that DLL4 may also be involved in cancer stem cell biology and that DLL4 antagonists may partially mediate anti-tumor effects through interactions with these cell types.

DLL4 is critically involved in arterial development. Its expression is primarily restricted to endothelial cells within normal tissue and it is upregulated in tumor vasculature (Duarte et al., Genes Dev. 2004, 18(20):2474-8; Patel et al., Cancer Res. 2005, 65(19):8690-7; Jubb et al., Am J. Pathol. 2010, 176(4):2019-28; Jubb et al., Br J Cancer 2009, 101(10):1749-57; Mailhos et al., Differentiation, 2001, 69(2-3):135-44). DLL4 is expressed in malignant epithelial cells of colonic adenomas and adenocarcinomas (Jubb et al., Br J Cancer 2009, 101(10):1749-57). Its expression has also been reported on the vasculature of tumors from human clear-cell renal cell carcinomas and cancers of the breast and bladder (Mailhos et al., Differentiation 2001, 69:135; Patel et al., Cancer Res. 2005, 65:8690; Patel et al., Clin. Cancer Res. 2006, 12:4836). And a recent study suggested that DLL4 may be expressed on a small proportion of tumor cells in human glioblastoma (Li et al. 2007, Cancer Res., 67, 11244). Overexpression of DLL4 in tumor cells causes activated Notch signaling in host stromal/endothelial cells, leading to increased blood vessel size and improved vascular function within tumors, which in turn leads to increased tumor growth rate (Li et al. Cancer Res. 2007, 67(23):11244-53). Conversely, inhibition of DLL4 causes non-productive angiogenesis and suppression of tumor growth (Noguera-Troise et al., Nature 2006, 444(7122):1032-7; Ridgway et al., Nature 2006, 444(7122):1083-7; Benedito et al., Cell 2009, 137(6):1124-35; Li &Harris, Cancer Cell 2005, 8(1):1-3; Li et al., Cancer Res. 2007, 67(23):11244-53; Hoey et al., Cell Stem Cell 2009, 5(2):168-77).

Blocking DLL4 signaling on tumor growth has been reported to reduce tumor growth in several preclinical models of cancer in which tumor cell lines are grown subcutaneously in immunodeficient mice (Ridgway et al., Nature 2006, 444(7122):1083-7; Noguera-Troise et al, Nature 2006, 444(7122):1032-7). The anti-tumor effects were associated with an increase in the density of poorly functional vessels in the tumors concomitant with an increase in hypoxia. DLL4 blockade with neutralizing antibodies also significantly delayed tumor growth and recurrence in human breast and colon xenograft models when combined with chemotherapy, presumably due to decreased tumor cell proliferation and cancer stem cell (CSC) frequency, as well as dysfunctional tumor angiogenesis (Hoey et al., Cell Stem Cell 2009, 5(2):168-77). Thus, DLL4 may also play a role in development of the tumor vasculature.

Ionizing radiation (IR) can also disrupt tumor vasculature. Delivery of a high single dose of IR (15 Gy) is sufficient to ablate endothelial cells within the irradiated field, which prevents subsequent tumor angiogenesis, and vasculogenesis mediated by the recruitment of bone marrow derived cells (mainly CD11b+) is required before tumor regrowth can occur (Ahn & Brown, Cancer Cell 2008, 13(3):193-205; Ahn et al., Proc Natl Acad Sci USA 2010, 107(18):8363-8). Administration of a CD11b+ blocking mAb, interferes with CD11b+ myelomonocyte recruitment, which delays tumor regrowth following an ablative dose of tumor irradiation (Ahn et al., Proc Natl Acad Sci USA 2010, 107(18):8363-8). BMDCs are recruited via stromal cell derived factor-1 (SDF-1), and pharmacological blockade of the SDF-1-CXCR4 interaction interferes with tumor regrowth following tumor irradiation (Kioi et al., J Clin Invest 2010, 120(3):694-705; Kozin et al., Cancer Res 2010, 70(14):5679-85). It is not yet known whether a lower dose of IR also induces CD11b+ recruitment to the tumor or what its relative contribution to the tumor vasculature would be, since tumor angiogenesis is not ablated at lower IR doses (and hence, vasculogenesis is not essential for tumor growth). In clinical radiotherapy, single dose IR is not commonly given at a dose high enough to cause ablation of tumor angiogenesis, with the exception being stereotactic radiosurgery.

Several approaches have been used to target tumor angiogenesis to enhance the effect of ionizing radiation (IR). VEGF's addition to radiation therapy enhances tumor growth delay in several preclinical xenograft models (Gorski et al., Cancer Res 1999, 59(14):3374-8; Lee et al., Cancer Res 2000, 60(19):5565-70). However, when Lee et al., combined anti-VEGF mAb with IR (20-40 Gy) for normoxic or hypoxic LS174T xenograft tumors, the effect on tumor growth delay was additive at best; the exception was seen only with the highest dose of IR (40 Gy) and hypoxic tumors (Lee et al., Cancer Res 2000, 60(19):5565-70). Due to the importance of tumor reoxygenation induced by VEGF pathway blockade, the timing and sequencing of IR may be important when the two therapies are used together (Winkler et al., Cancer Cell 2004, 6(6):553-63; Williams et al., Clin Cancer Res. 2004, 10(24):8587-93).

There is also evidence to suggest that ionizing radiation can affect the Notch pathway in endothelial cells as well as human breast cancer and gliomas (Phillips et al., J Natl Cancer Inst. 2006, 98(24):1777-85; Scharpfenecker et al., Int J Radiat Oncol Biol Phys. 2009, 73(2):506-13; Imaizumi et al., PLoS One. 2010, 5(6):e11084; Wang et al., Stem Cells. 2009, 28(1): 17-28). Tumors that are resistant to anti-VEGF therapy are responsive to DLL4 blockade with blocking monoclonal antibodies or a DLL4 extracellular domain-FC decoy protein. (Ridgway et al., Nature 2006, 444(7122):1083-7; Li et al., Cancer Res. 2007, 67(23):11244-53.) However, there are no published reports examining DLL4 blockade within the tumor and its vasculature in combination with IR.

It is accordingly an object of the invention to provide a combination therapy in which DLL4 blockade is used together with IR for the treatment or inhibition of cancer, neoplastic disease, tumor cell growth or proliferation, tumor metastasis, or related conditions.

SUMMARY OF THE INVENTION

In accordance with the invention, some embodiments of the invention provide methods of treating cancer in a human comprising administering a therapeutically effective amount of ionizing radiation and an anti-DLL4 antibody or a DLL4-binding fragment thereof, wherein the anti-DLL4 antibody or DLL4-binding fragment antagonizes the biological activity of DLL4.

In other embodiments of the invention, there is provided methods of reducing or inhibiting tumor cell proliferation or tumor angiogenesis in a human comprising administering a therapeutically effective amount of ionizing radiation and an anti-DLL4 antibody or a DLL4-binding fragment thereof, wherein the anti-DLL4 antibody or the DLL4-binding fragment antagonizes the biological activity of DLL4.

In still other embodiments, there is provided methods of reducing malignant tumor cell invasion or metastasis in a human comprising administering a therapeutically effective amount of ionizing radiation and an anti-DLL4 antibody or a DLL4-binding fragment thereof, wherein the anti-DLL4 antibody or the DLL4-binding fragment antagonizes the biological activity of DLL4.

Other embodiments provide methods of reducing or inhibiting a neoplasia in a human comprising administering a therapeutically effective amount of ionizing radiation and an anti-DLL4 antibody or a DLL4-binding fragment thereof, wherein the anti-DLL4 antibody or the DLL4-binding fragment antagonizes the biological activity of DLL4.

In some embodiments, methods of delaying tumor regrowth in a subject following treatment with at least one dose of ionizing radiation comprising administering to the subject a therapeutically effective amount of an anti-DLL4 antibody or a DLL4-binding fragment thereof, wherein the anti-DLL4 antibody or the DLL4-binding fragment antagonizes the biological activity of DLL4.

In some embodiments, the cancer, tumor, or neoplasia is colorectal cancer, metastatic colon cancer, colon cancer, rectal cancer, glioblastoma, breast cancer, non-small cell lung cancer, head and neck cancer, renal cell carcinoma, cervical cancer, ovarian cancer, or prostate cancer.

In some embodiments, the anti-DLL4 antibody or the DLL4-binding fragment thereof is human.

In some embodiments, the anti-DLL4 antibody or DLL4-binding fragment thereof comprises a heavy chain variable domain comprising amino acid sequences CDR1 as set forth in SEQ ID NO:1, CDR2 as set forth in SEQ ID NO:2, and CDR3 as set forth in SEQ ID NO:3; and a light chain variable domain comprising amino acid sequences CDR1 as set forth in SEQ ID NO:4, CDR2 as set forth in SEQ ID NO:5, and CDR3 as set forth in SEQ ID NO:6.

In some embodiments, the anti-DLL4 antibody or DLL4-binding fragment thereof comprises a heavy chain variable domain as set forth in SEQ ID NO: 7; and a light chain variable domain as set forth in SEQ ID NO: 8.

In some embodiments, the dose of the anti-DLL4 antibody or DLL4-binding fragment thereof is about 0.1 to about 10 mg/kg.

In some embodiments, the anti-DLL4 antibody or DLL4-binding fragment thereof is administered twice per week.

In some embodiments, the anti-DLL4 antibody or DLL4-binding fragment thereof is administered following the first dose of ionizing radiation administered.

In some embodiments, the anti-DLL4 antibody or DLL4-binding fragment thereof is administered before the first dose of ionizing radiation is administered.

In some embodiments, the anti-DLL4 antibody or DLL4-binding fragment thereof is administered on the same day as the first dose of ionizing radiation is administered.

In some embodiments, the total dose of ionizing radiation is about 45 Gy to about 80 Gy.

In some embodiments, the ionizing radiation is administered in fractionated doses of from about 1.5 to about 3.5 Gy/day.

In some embodiments, the ionizing radiation is palliative and the total dose of ionizing radiation is about 8 Gy to about 60 Gy.

In some embodiments, the ionizing radiation is administered in fractionated doses of from about 3 to about 8 Gy/day.

In some embodiments, the method further comprises administering a chemotherapeutic drug.

It is to be understood that both the foregoing general description and the following detailed description are exemplary and explanatory only and are not restrictive of the invention as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 1C depicts the fold change in luciferase activity in LS174T Notch-luc cells incubated on BSA or DLL4-coated plates in the presence of DMSO (vehicle), isotype IgG1, DBZ, or DLL4 mAb for 24 hr. The upper panel presents the change in bar graph form while the bottom panel shows a 'heat map' of Notch luciferase activity.

FIG. 8A presents western blots for untreated LS174T and FaDu cells for expression of DLL4, Jag 1, Notch-1 to 4 receptors.

FIG. 10A shows images taken at 400× of TUNEL staining of tumor sections from mice treated as indicated.

DETAILED DESCRIPTION OF THE EMBODIMENTS

Figure 1A:
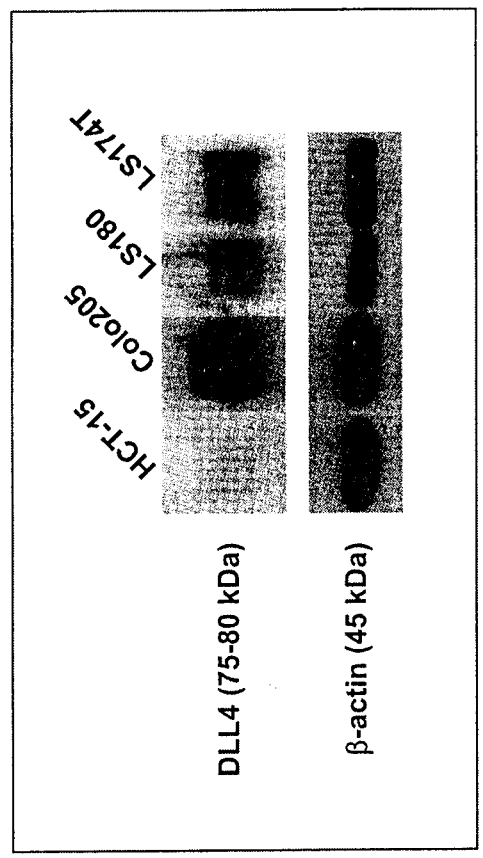
FIG. 1A depicts a DLL4 immunoblot of human colorectal carcinoma cell lines.

Reference will now be made in detail to the present embodiments of the invention.

According to one aspect of the invention there is provided a method of treating cancer in an animal by administering a therapeutically effective amount of an antibody that antagonizes the biological activity of DLL4 in combination with other antibodies or chemotherapeutic drugs or radiation therapy. The method may include selecting an animal in need of treatment for cancer, and administering to the animal a therapeutically effective amount of an antibody that antagonizes the biological activity of DLL4. In one embodiment the invention provides a method of treating cancer in a human by administering ionizing radiation and a therapeutically effective amount of an antibody that antagonizes the biological activity of DLL4.

According to another aspect there is provided a method of reducing or inhibiting tumor cell proliferation or tumor angiogenesis, in an animal by administering a therapeutically effective amount of an antibody that antagonizes the biological activity of DLL4 in combination with other antibodies or chemotherapeutic drugs or radiation therapy. The method may include selecting an animal in need of reducing or inhibiting tumor cell proliferation or angiogenesis, and administering to the animal a therapeutically effective amount of an antibody that antagonizes the biological activity of DLL4. In one embodiment the invention provides a method of reducing or inhibiting tumor cell proliferation or tumor angiogenesis in a human by administering a therapeutically effective amount of ionizing radiation and an antibody that antagonizes the biological activity of DLL4.

According to another aspect there is provided a method of reducing malignant tumor cell invasion or metastasis in an animal by administering a therapeutically effective amount of an antibody that antagonizes the biological activity of DLL4 in combination with other antibodies or chemotherapeutic drugs or radiation therapy. The method may include selecting an animal in need of reducing malignant tumor cell invasion or metastasis, and administering to the animal a therapeutically effective amount of an antibody that antagonizes the biological activity of DLL4. In one embodiment the invention provides a method of reducing malignant tumor cell invasion or metastasis in a human by administering a therapeutically effective amount of ionizing radiation and an antibody that antagonizes the biological activity of DLL4.

According to another aspect there is provided a method of reducing or inhibiting a neoplasia in an animal by administering a therapeutically effective amount of an antibody that antagonizes the biological activity of DLL4 in combination with other antibodies or chemotherapeutic drugs or radiation therapy. The method may include selecting an animal in need of treating a neoplasia, and administering to the animal a therapeutically effective amount of an antibody that antagonizes the biological activity of DLL4. In one embodiment the invention provides a method of reducing or inhibiting a neoplasia in a human by administering a therapeutically effective amount of ionizing radiation and an antibody that antagonizes the biological activity of DLL4.

A malignant tumor may be chosen from melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, cancer of the rectum, cancer of the anal canal, pancreatic cancer, esophageal carcinoma, head and neck cancers, mesothelioma, sarcomas, biliary (cholangiocarcinoma), small bowel adenocarcinoma, pediatric malignancies or epidermoid carcinoma.

Treatable proliferative or angiogenic diseases include neoplastic diseases, such as, melanoma, small cell lung cancer, non-small cell lung cancer, glioma, hepatocellular (liver) carcinoma, thyroid tumor, gastric (stomach) cancer, gallbladder cancer, prostate cancer, breast cancer, ovarian cancer, bladder cancer, lung cancer, glioblastoma, endometrial cancer, kidney cancer, colon cancer, cancer of the rectum, cancer of the anal canal, pancreatic cancer, ovarian, esophageal carcinoma, head and neck cancers, mesothelioma, sarcomas, biliary (cholangiocarcinoma), small bowel adenocarcinoma, pediatric malignancies, epidermoid carcinoma and leukemia, including chronic myelogenous leukemia.

According to another aspect of the invention there is provided the use of an antibody that antagonizes the biological activity of DLL4 in combination with other antibodies or chemotherapeutic drugs or radiation therapy for the manufacture of a medicament for the treatment of cancer in a mammal. In one embodiment, the use is in combination with ionizing radiation.

According to another aspect of the invention there is provided an antibody that antagonizes the biological activity of DLL4 in combination with other antibodies or chemotherapeutic drugs or radiation therapy for use as a medicament for the treatment of cancer in a mammal. In one embodiment, the use is in combination with ionizing radiation.

According to another aspect there is provided the use of an antibody that antagonizes the biological activity of DLL4 in combination with other antibodies or chemotherapeutic drugs or radiation therapy for the manufacture of a medicament for the reduction or inhibition of tumor cell proliferation or tumor angiogenesis in an animal. In one embodiment, the use is in combination with ionizing radiation.

According to another aspect there is provided an antibody that antagonizes the biological activity of DLL4 in combination with other antibodies or chemotherapeutic drugs or radiation therapy for use as a medicament for the reduction or inhibition of tumor cell proliferation or tumor angiogenesis in an animal. In one embodiment, the use is in combination with ionizing radiation.

According to another aspect there is provided the use of an antibody that antagonizes the biological activity of DLL4 in combination with other antibodies or chemotherapeutic drugs or radiation therapy for the manufacture of a medicament for reducing malignant tumor cell invasion or metastasis in an animal. In one embodiment, the use is in combination with ionizing radiation.

According to another aspect there is provided an antibody that antagonizes the biological activity of DLL4 in combination with other antibodies or chemotherapeutic drugs or radiation therapy for use as a medicament for reducing malignant tumor cell invasion or metastasis in an animal. In one embodiment, the use is in combination with ionizing radiation.

According to another aspect there is provided the use of an antibody that antagonizes the biological activity of DLL4 in combination with other antibodies or chemotherapeutic drugs or radiation therapy for the manufacture of a medicament for reducing or inhibiting a neoplasia in an animal. In one embodiment, the use is in combination with ionizing radiation.

According to another aspect there is provided an antibody that antagonizes the biological activity of DLL4 in combination with other antibodies or chemotherapeutic drugs or radiation therapy for use as a medicament for reducing or inhibiting a neoplasia in an animal. In one embodiment, the use is in combination with ionizing radiation.

In one embodiment, the present invention is suitable for use in antagonizing DLL4 in patients with a tumor that is dependent alone, or in part, on DLL4.

In one embodiment, the present invention is suitable for use in antagonizing DLL4 in patients in which the cancer, tumor, or neoplasia expresses DLL4

In another embodiment, the present invention is suitable for use in antagonizing DLL4 in patients in which the cancer, tumor, or neoplasia does not express DLL4.

According to another aspect of the invention there is provided a pharmaceutical composition comprising, consisting essentially of, or consisting of an antibody that antagonizes the biological activity of DLL4 in combination with other antibodies or chemotherapeutic drugs or radiation therapy, and a pharmaceutically acceptable carrier. In one embodiment the anti-DLL4 antibody is a fully human antibody. In one embodiment the anti-DLL4 antibody is chosen from the 4B4, 2H10, 21F7, 12A1, 17F3, 9G8, 20G8, 21H3, 1E4, 3A7, 4B3, 1D4, antibodies described in US2010/0196385 or WO 2010/032060, or combinations of those antibodies, or DLL4-binding fragments thereof. In one embodiment, the antibody is provided as a pharmaceutical composition in a kit that includes instructions for administering the antibody in combination with ionizing radiation.

In one embodiment, an anti-DLL4 antibody or DLL4-binding fragment thereof comprises a variable heavy chain amino acid sequence comprising CDR1, CDR2, and CDR3 amino acid sequences as set forth in SEQ ID NO:1, SEQ ID NO: 2, and SEQ ID NO: 3, respectively, and a variable light chain amino acid sequence comprising CDR1, CDR2, and CDR3 amino acid sequences as set forth in SEQ ID NO: 4, SEQ ID NO: 5, and SEQ ID NO: 6, respectively.

In another embodiment, an anti-DLL4 antibody, or antigen-binding portion thereof, comprises a heavy chain polypeptide comprising the sequence of SEQ ID NO: 7. In another embodiment, an anti-DLL4 antibody, or antigen-binding portion thereof, further comprises a light chain polypeptide comprising the sequence of SEQ ID NO:8. In some embodiments, the antibody is a fully human monoclonal antibody.

In another embodiment, an anti-DLL4 antibody or DLL4-binding fragment comprises a variable heavy chain amino acid sequence comprising at least one, at least two, or at least three of the CDRs of the antibody encoded by the polynucleotide in plasmid designated Mab21H3VH which was deposited at the American Type Culture Collection (ATCC) under number PTA-9501 on Sep. 17, 2008.

In another embodiment, an anti-DLL4 antibody or DLL4-binding fragment comprises a variable light chain amino acid sequence comprising at least one, at least two, or at least three of the CDRs of the antibody encoded by the polynucleotide in plasmid designated Mab21H3VLOP which was deposited at the American Type Culture Collection (ATCC) under number PTA-9500 on Sep. 17, 2008.

It is noted that those of ordinary skill in the art can readily accomplish CDR determinations. See for example, Kabat et al., Sequences of Proteins of Immunological Interest, Fifth Edition, NIH Publication 91-3242, Bethesda Md. (1991), vols. 1-3. Kabat provides multiple sequence alignments of immunoglobulin chains from numerous species antibody isotypes. The aligned sequences are numbered according to a single numbering system, the Kabat numbering system. The Kabat sequences have been updated since the 1991 publication and are available as an electronic sequence database (latest downloadable version 1997). Any immunoglobulin sequence can be numbered according to Kabat by performing an alignment with the Kabat reference sequence. Accordingly, the Kabat numbering system provides a uniform system for numbering immunoglobulin chains.

In some embodiments, following administration of the antibody that specifically binds to DLL4, a clearing agent is administered, to remove excess circulating antibody from the blood.

Anti-DLL4 antibodies in combination with other antibodies or chemotherapeutic drugs or radiation therapy are useful in treating symptoms resulting from DLL4 induced cell adhesion, invasion, angiogenesis, proliferation and/or intracellular signaling. Further embodiments involve using the antibodies and methods described herein to treat cell adhesion, invasion, angiogenesis and/or proliferation-related diseases including neoplastic diseases, such as, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, cancer of the rectum, cancer of the anal canal, and pancreatic cancer.

In one embodiment, an anti-DLL4 antibody in combination with other antibodies or chemotherapeutic drugs or radiation therapy has therapeutic effects in treating solid tumors whose development relies on a small population of stem cells with the capacity to proliferate and efficiently give rise both to additional tumor stem cells, e.g., acute myeloid leukemia (AML) and breast tumors.

Further embodiments, features, and the like regarding methods comprising using an anti-DLL4 antibody in combination with a second therapy as disclosed herein are provided in additional detail below.

DEFINITIONS

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually.

The term "DLL4" refers to the molecule that is DLL4 protein, also known as Delta-like protein 4 precursor, *Drosophila* Delta homolog 4, hdelta2, MGC126344, or UNQ1895/PRO4341.

An "antagonist of the biological activity of DLL4" is capable of eliminating, reducing or significantly reducing the activity of DLL4. An "antagonist of the biological activity of DLL4" is capable of eliminating, reducing or significantly reducing DLL4 signaling. An "antagonist of the biological activity of DLL4" may eliminate or significantly reduce angiogenesis and/or proliferation.

By way of example, an antagonist of the biological activity of DLL4 may be an antibody or fragment thereof that binds DLL4. Examples of anti-DLL4 antibodies suitable for use in the practice of the methods of the invention are described in the Examples and are also described in US 2010/0196385, "Targeted Binding Agents Directed to DLL4 and Uses Thereof" by Vehe Bedian, David Jenkins, and Ian Foltz, which also published as WO 2010/032060. Each of those publications is incorporated by reference in its entirety. Thus, an antagonist of the biological activity of DLL4 may be any isolated antibody, or binding fragment thereof, that specifically binds to DLL4, wherein the antibody exhibits one or more of the following properties, comprising: binds human DLL4 with a $K_D$ of less than 200 pM; cross-reacts with cynomologus monkey DLL4; weakly cross-reacts with mouse DLL4; binds cynomologus DLL4 with nearly equivalent affinity; does not bind significantly to DLL1 or Jagged 1; exhibits over 85% reverse DLL4-stimulated inhibition of HUVEC cell proliferation in 2D culture compared to a control; exhibits greater than 50% inhibition of HUVEC cell tube formation in 2D culture at a concentration of 0.08 μg/ml relative to a control; and exhibits less than 50% internalization at four hours relative to t=0 control.

One example of an anti-DLL4 antibody suitable for use in the invention is the human antibody 21H3RK, described in US2010/0196385 or WO 2010/032060. 21 H3RK is a human anti-human DLL4 antibody that demonstrates minimal binding to human Jagged-1 or human DLL1. When tested in an IgG1 format, it was an effective inhibitor of both HUVEC proliferation and endothelial cell tube formation in vitro. 21H3RK was also active when tested in vivo using a spheroid-based assay of angiogenesis. The 21H3RK epitope has been mapped to the DSL and EGF1 domains of DLL4, localizing within amino acids 147-224 (AA 187-201) of DLL4. The amino acid sequence of the variable region of the heavy chain of 21H3RK is set forth in SEQ ID NO: 30 of US2010/0196385, while the amino acid sequence of the variable region of the light chain of 21H3RK is set forth in SEQ ID NO: 50.

Another example of anti-DLL4 antibody or DLL4-binding fragment thereof suitable for use in the invention is an anti-DLL4 antibody of DLL4-binding fragment thereof that comprises a heavy chain variable domain comprising CDR1: NYGIT; CDR2: WISAYNGNTNYAQKLQD; and CDR3: DRVPRIPVTTEAFDI amino acid sequences as set forth in SEQ ID NO:1, SEQ ID NO: 2, and SEQ ID NO: 3, respectively, and a light chain variable domain comprising CDR1: SGSSSNIGSYFVY; CDR2: RNNQRPS; and CDR3: AAWDDSLSGHWV amino acid sequences as set forth in SEQ ID NO:4, SEQ ID NO: 5, and SEQ ID NO: 6, respectively. In one embodiment, an anti-DLL4 antibody or DLL4-binding fragment comprises a heavy chain variable domain as set forth in SEQ ID NO: 7 and a light chain variable domain as set forth in SEQ ID NO: 8.

SEQ ID NO: 7
Gln Val Gln Leu Val Gln Ser Gly Ala Glu Val Lys

Lys Pro Gly Ala Ser Val Lys Val Ser Cys Lys Ala

Ser Gly Tyr Thr Phe Thr Asn Tyr Gly Ile Thr Trp

Val Arg Gln Ala Pro Gly Gln Gly Pro Glu Trp Met

Gly Trp Ile Ser Ala Tyr Asn Gly Asn Thr Asn Tyr

Ala Gln Lys Leu Gln Asp Arg Val Thr Val Thr Thr

Asp Thr Ser Thr Ser Thr Ala Tyr Met Glu Leu Arg

Ser Leu Arg Ser Asp Asp Thr Ala Val Tyr Tyr Cys

Ala Arg Asp Arg Val Pro Arg Ile Pro Val Thr Thr

Glu Ala Phe Asp Ile Trp Gly Gln Gly Thr Met Val

Thr Val Ser Ser

SEQ ID NO: 8
Gln Ser Val Leu Thr Gln Pro Pro Ser Ala Ser Gly

Thr Pro Gly Gln Arg Val Thr Ile Ser Cys Ser Gly

Ser Ser Ser Asn Ile Gly Ser TyrPhe Val Tyr Trp

Tyr Gln Gln Leu Pro Gly Thr Ala Pro Lys Leu Leu

Ile Tyr Arg Asn Asn Gln Arg Pro Ser Gly Val Pro

Asp Arg Phe Ser Gly Ser Glu Ser Gly Thr Ser Ala

Ser Leu Ala Ile Ser Gly Leu Arg Ser Glu Asp Glu

Ala Asp Tyr Tyr Cys Ala Ala Trp Asp Asp Ser Leu

Ser Gly His Trp Val Phe Gly Gly Gly Thr Lys Leu

Thr Val Leu

Still other examples of alternative (or additional) anti-DLL4 antibodies suitable for use in the invention include antibodies, 4B4, 2H10, 21F7, 21 H3, 12A1, 17F3, 9G8, 20G8, 1E4, 3A7, 4B3, 1D4, described in US2010/0196385 or WO 2010/032060, or combinations of those antibodies or binding fragments thereof. Any of those antibodies or binding fragments may also be used in combination with the 21H3RK antibody or with a DLL4-binding fragment thereof.

"Active" or "activity" in regard to an DLL4 polypeptide refers to a portion of an DLL4 polypeptide that has a biological or an immunological activity of a native DLL4 polypeptide. "Biological" when used herein refers to a biological function that results from the activity of the native DLL4 polypeptide. DLL4 biological activity includes, for example, DLL4 induced cell adhesion and invasion and/or angiogenesis and/or proliferation.

Unless otherwise specified, an antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, or a fully human antibody. A "human antibody" is an antibody derived from a human or an antibody obtained from a transgenic organism that has been engineered to produce human antibodies in response to antigenic challenge. A human antibody is also an antibody wherein the heavy and light chains are encoded by a nucleotide sequence derived from one or more sources of human DNA. A fully human antibody can be constructed by genetic or chromosomal transfection methods, phage display technology (e.g., U.S. Pat. No. 5,969,108), or in vitro activated B cells (e.g., U.S. Pat. Nos. 5,567,610 and 5,229,275). An antibody may be from any species.

As used herein, the terms "antibody" and "antibodies" (immunoglobulins) encompass monoclonal antibodies (including full-length monoclonal antibodies), polyclonal antibodies, camelised antibodies and chimeric antibodies. The term "antibody" or "antibodies" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen chain. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK. The term "variable region" may also be used to describe the variable domain of a heavy chain or light chain. Particular amino acid residues are believed to form an interface between the light and heavy chain variable domains. The variable regions of each light/heavy chain pair form an antibody binding site. Such antibodies may be derived from any mammal, including, but not limited to, humans, monkeys, pigs, horses, rabbits, dogs, cats, mice, etc.

The term "antibody" or "antibodies" includes binding fragments of the antibodies of the invention, exemplary fragments include single-chain Fvs (scFv), single-chain antibodies, single domain antibodies, domain antibodies, Fv fragments, Fab fragments, F(ab') fragments, F(ab')$_2$ fragments, antibody fragments that exhibit the desired biological activity, disulfide-stabilised variable region (dsFv), dimeric variable region (Diabody), anti-idiotypic (anti-Id) antibodies, intrabodies, linear antibodies, single-chain antibody molecules and multispecific antibodies formed from antibody fragments and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "mAb" refers to a monoclonal antibody.

It has been shown that fragments of a whole antibody can perform the function of binding antigens. Examples of binding fragments are (Ward, E. S. et al., (1989) Nature 341, 544-546) the Fab fragment consisting of VL, VH, CL and CH1 domains; (McCafferty et al (1990) Nature, 348, 552-554) the Fd fragment consisting of the VH and CH1 domains; (Holt et al (2003) Trends in Biotechnology 21, 484-490) the Fv fragment consisting of the VL and VH domains of a single antibody; (iv) the dAb fragment (Ward, E. S. et al., Nature 341, 544-546 (1989); McCafferty et al (1990) Nature, 348, 552-554; Holt et al (2003) Trends in Biotechnology 21, 484-490), which consists of a VH or a VL domain; (v) isolated CDR regions; (vi) F(ab').sub.2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, (1988) Science, 242, 423-426; Huston et al, (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger, P. (1993) et al, Proc. Natl. Acad. Sci. USA 90 6444-6448). Fv, scFv or diabody molecules may be stabilised by the incorporation of disulphide bridges linking the VH and VL domains (Reiter, Y. et al, Nature Biotech, 14, 1239-1245, 1996). Minibodies comprising a scFv joined to a CH3 domain may also be made (Hu, S. et al, (1996) Cancer Res., 56, 3055-3061). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

"Binding fragments" of an antibody are produced by recombinant DNA techniques, or by enzymatic or chemical cleavage of intact antibodies. Binding fragments include Fab, Fab', F(ab)$_2$, Fv, dAb and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

The term "epitope" includes any protein determinant capable of specific binding to an immunoglobulin. Epitopic determinants usually consist of chemically active surface groupings of molecules such as amino acids or sugar side chains and may, but not always, have specific three-dimensional structural characteristics, as well as specific charge characteristics. An antibody is said to "specifically bind" an antigen when the dissociation constant is less than or equal to 1 µM, less than or equal to 100 nM, or less than or equal to 10 nM.

The term "isotype" refers to the classification of an antibody's heavy or light chain constant region. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2 (gamma 2), IgG3 (gamma 3), and IgG4 (gamma 4), and IgA1 and IgA2. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate in humans. Human light chain constant regions may be classified into two major classes, kappa and lambda.

If desired, the isotype of an antibody that specifically binds DLL4 can be switched, for example to take advantage of a biological property of a different isotype. For example, in some circumstances it can be desirable that the antibodies be capable of fixing complement and participating in complement-dependent cytotoxicity (CDC). There are a number of isotypes of antibodies that are capable of the same, including, without limitation, the following: murine IgM, murine IgG2a, murine IgG2b, murine IgG3, human IgM, human IgA, human IgG1, and human IgG3. In other embodiments it can be desirable that the antibodies be capable of binding Fc receptors on effector cells and participating in antibody-dependent cytotoxicity (ADCC). There are a number of isotypes of antibodies that are capable of the same, including, without limitation, the following: murine IgG2a, murine IgG2b, murine IgG3, human IgG1, and human IgG3. It will be appreciated that antibodies can be isotype switched using conventional techniques that are well known in the art. Such techniques include the use of direct recombinant techniques (see e.g., U.S. Pat. No. 4,816,397), cell-cell fusion techniques (see e.g., U.S. Pat. Nos. 5,916,771 and 6,207,418), among others.

By way of example, the anti-DLL4 antibodies discussed herein are fully human antibodies. If an antibody possessed desired binding to DLL4, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC and/or be capable of binding to Fc receptors on effector cells and participating in ADCC.

"Mammal" when used herein refers to any animal that is considered a mammal. Preferably, the mammal is human.

"Animal" when used herein encompasses animals considered a mammal. Preferably the animal is human.

The term "patient" includes human and veterinary subjects.

The term "agent" is used herein to denote a chemical compound, a mixture of chemical compounds, a biological macromolecule, or an extract made from biological materials.

The term "pharmaceutical agent or drug" as used herein refers to a chemical compound or composition capable of inducing a desired therapeutic effect when properly administered to a patient. Other chemistry terms herein are used according to conventional usage in the art, as exemplified by The McGraw-Hill Dictionary of Chemical Terms (Parker, S., Ed., McGraw-Hill, San Francisco (1985)), (incorporated herein by reference).

A "therapeutically effective" amount as used herein is an amount that provides some improvement or benefit to the subject. Stated in another way, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject.

Embodiments of the invention include sterile pharmaceutical formulations of anti-DLL4 antibodies that are useful as treatments for diseases in combination with other antibodies or chemotherapeutic drugs or radiation therapy. Such formulations would inhibit the binding of a native DLL4 to the Notch 1 or Notch 4 receptor, thereby effectively treating pathological conditions where, for example, serum or tissue DLL4 expression is abnormally elevated. Anti-DLL4 antibodies preferably possess adequate affinity to potently inhibit native DLL4 binding to the Notch 1 or Notch 4 receptor and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilization and reconstitution of the antibody. Antibodies ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, direct injection to a tumor site, or by sustained release systems as noted below. In some embodiments, an antibody is administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibodies of the invention to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.0001 mg/kg, 0.001 mg/kg, 0.01 mg/kg, 0.1 mg/kg, 1 mg/kg, 10 mg/kg up to 100 mg/kg, 1000 mg/kg, 10000 mg/kg or more, of the patient's body weight depending on the factors mentioned above. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight depending on the factors mentioned above. For example, an antibody of the invention may be administered in a dosage of about 0.1 to about 10 mg/kg. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. See also Baldrick P. "Pharmaceutical excipient development: the need for preclinical guidance." Regul. Toxicol. Pharmacol. 32(2):210-8 (2000); Wang W. "Lyophilization and development of solid protein pharmaceuticals." Int. J. Pharm. 203 (1-2):1-60 (2000); Charman W N "Lipids, lipophilic drugs, and oral drug delivery-some emerging concepts." J Pharm Sci. 89(8):967-78 (2000); Powell et al. "Compendium of excipients for parenteral formulations" PDA J Pharm Sci Technol. 52:238-311 (1998) and the citations therein for additional information related to formulations, excipients and carriers well known to pharmaceutical chemists.

Doses of antibodies of the invention may be repeated and the frequency of the dosing may be adjusted to maximize therapeutic benefit while minimizing any undesirable effect. For example, antibodies of the invention may be administered daily, on alternate days, twice per week, or weekly. Some non-limiting dosing schedules are provided elsewhere in the disclosure in the context of specific therapies and in the Examples.

An anti-DLL4 antibodies described may be applied in combination with one or more of radiotherapy, additional antibody or other biologic-based therapy, conventional surgery, or chemotherapy.

In one aspect of the invention, an anti-DLL4 antibody therapy is used in combination with radiation treatment, also called radiotherapy. Various types of radiotherapy are available and the selection of a particular radiotherapy is generally dependent upon the nature of the cancer, tumor, or neoplasia to be treated. The three main types of radiotherapy are external beam radiotherapy (EBRT or XRT) or teletherapy, brachytherapy or sealed source radiotherapy, and systemic radioisotope therapy or unsealed source radiotherapy. The differences relate to the position of the radiation source; external is outside the body, brachytherapy uses sealed radioactive sources placed precisely in the area under treatment, and systemic radioisotopes are given by infusion or oral ingestion. Brachytherapy can use temporary or permanent placement of radioactive sources.

Internally administered radiotherapy can be accomplished by linking a radionuclide to an antibody, hormone, or other targeting molecule, or to implantable materials such as beads, rods, seeds, or removable catheter. Radionuclides (radioisotopes) that may be used include $^{3}H$, $^{14}C$, $^{15}N$, $^{35}S$, $^{89}Sr$, $^{90}Y$, $^{99}TC$, $^{103}Pd$, $^{111}In$, $^{125}I$, $^{131}I$, $^{153}Sm$, $^{192}Ir$.

The term "ionizing radiation" (IR) refers to X-rays, gamma rays (e.g., emitted by radium, uranium or cobalt 60), and particle beam radiation (e.g., protons, neutrons, pions or heavy ions). Radiation treatment doses when utilizing X-ray or gamma radiation may be within a range of about 0.01-100 Gray ("Gy"), within a range of about 0.1-80 Gy, within a range of about 1-10 Gy, within a range of 0.5-10 Gy or within a range of 1-5 Gy. Generally, multiple dose administrations of radiation are administered to a patient over a course of treatment. Total doses of radiation treatment over a complete course of treatment may be within a range of 1-100 Gy, 1-90 Gy, 1-80 Gy, 1-70 Gy, 1-60 Gy, 1-50 Gy, 1-40 Gy, 1-30 Gy, 1-20 Gy, 1-10 Gy, 1-5 Gy, 8-100 Gy, 8-90 Gy, 8-80 Gy, 8-70 Gy, 8-60 Gy, 8-50 Gy, 8-40 Gy, 8-30 Gy, 8-20 Gy, 8-10 Gy, 10-100 Gy, 10-90 Gy, 10-80 Gy, 10-70 Gy, 10-60 Gy, 10-50 Gy, 10-40 Gy, 10-30 Gy, 10-20 Gy, 20-100 Gy, 20-90 Gy, 20-80 Gy, 20-70 Gy, 20-60 Gy, 20-50 Gy, 20-40 Gy, 20-30 Gy, 30-100 Gy, 30-90 Gy, 30-80 Gy, 30-70 Gy, 30-60 Gy, 30-50 Gy, 30-40 Gy, 40-100 Gy, 40-90 Gy, 40-80 Gy, 40-70 Gy, 40-60 Gy, 40-50 Gy, 50-100 Gy, 50-90 Gy, 50-80 Gy, 50-70 Gy, 50-60 Gy, 60-100 Gy, 60-90 Gy, 60-80 Gy, 60-70 Gy, 70-100 Gy, 70-90 Gy, 70-80 Gy, 80-100 Gy, 80-90 Gy, 90-100 Gy, about 1 Gy, about 5 Gy, about 8 Gy, about 10 Gy, about 20 Gy, about 30 Gy, about 40 Gy, about 50 Gy, about 60 Gy, about 70 Gy, about 80 Gy, about 90 Gy, or about 100 Gy. The effective amount varies depending on the type and stage of cancer being treated. For curative (radical) cases, the typical dose for a solid epithelial tumor ranges from about 60 to about 80 Gy while lymphoma tumors are treated with 20 to 40 Gy, typically in 1.8 to 2 Gy fractions. Adjuvant doses are typically around 45-60 Gy in 1.8 to 2 Gy fractions. For palliative therapy, doses are typically around 30 to 60 Gy, typically in 5 to 10 fractions of about 3 to 8 Gy/fraction, for example, about 5 Gy/fraction. For example, palliative therapy may comprise a total dose of about 8 Gy, administered as a single dose, or it may comprise a total dose of 20 Gy administered in 5 Gy fractions, or it may comprise a total dose of 30 Gy administered in 3 Gy fractions. Many other factors may be considered when selecting a dose, including whether the patient is receiving chemotherapy, whether radiation therapy is being administered before or after surgery, and the degree of success of surgery.

In some embodiments, the radiation will be delivered in doses of 2-8, 2-6, 3-5, 4-6, or about 5 Gy per day. Further it may be delivered at a rate of 0.25 to 6 Gy per minute. Ionizing radiation may be in a total dose of 2-20 Gy in one day, or in fractions in different days in the range of 0.1 to 6 Gy per day and up to 30 days. Other examples of fractionated doses that may be used are described herein in the context of particular therapies. A typical fractionation schedule for adults is 1.8 to 2 Gy per day, five days a week. For children, a typical fraction size may be 1.5 to 1.8 Gy per day. In some cases, two fractions per day are used near the end of a course of treatment, particularly for tumors that regenerate more quickly when they are smaller, such as head-and-neck tumors. Other fractionation schedules include Continuous Hyperfractionated Accelerated Radiotherapy (CHART), for lung cancer, and Accelerated Partial Breast Irradiation (APBI), for breast cancer. CHART consists of three smaller fractions per day. APBI normally involves two high-dose fractions per day for five days, compared to whole breast irradiation, in which a single, smaller fraction is given five times a week over a six-to-seven-week period. Accelerated fractionation, in which regular doses are given 2-3 times per day, may also be used.

The radiation may be directed to the tumor by any guidance procedure, typically involving computed tomography (or CT) images taken shortly before treatment. The patient's body is often marked on the skin to indicate where the radiation should be directed. In some centers, the patient also is positioned to lie in a body mold as an extra measure to try to make sure the tumor is in the location indicated by the earlier CT scans. A margin around the tumor is generally included in the radiation target area to avoid missing any part of a tumor.

Carlos A Perez & Luther W Brady: Principles and Practice of Radiation Oncology, 2nd Ed. JB Lippincott Co, Phila, 1992, describes radiation therapy protocols and parameters which can be used in the present invention. For glioblastoma, Simpson W. J. et al., Int J Radiat Oncol Biol Phys (1993) 26:239-244 describes clinical protocols useful in the methods of the present invention. Similarly, Borgelt et al., Int J Radiat Oncol Biol Phys (1980) 6:1-9, describes clinical protocols useful in the methods of the present invention. Other considerations for incorporating antiangiogenic therapy into clinical protocols that include radiation therapy are discussed in Senan & Smit, The Oncologist, (2007) 12:456-77.

In those embodiments involving combination therapy, the conjoint treatment may be achieved by way of the simultaneous, sequential, or separate dosing of the individual components of the treatment. Examples of dosing schedules are presented herein, including in the Examples. When an anti-DLL4 antibody is used in combination with another product, or pharmaceutically acceptable salts thereof, it is used within the dosage range described herein and the other pharmaceutically active agent within its approved dosage range.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s). Further, "combination" therapy or treatment does not require (but does not exclude) simultaneous therapy. For example, in those embodiments in which radiotherapy is combined with anti-DLL4 antibody treatment, the radiotherapy may precede an anti-DLL4 antibody treatment, it may be administered concurrently with an anti-DLL4 antibody treatment, it may be administered on the same day as an anti-DLL4 antibody treatment, or it may be administered following an anti-DLL4 antibody treatment. Additional details regarding treatment sequences are provided in the context of specific therapies and in the Examples.

In one embodiment, the combined therapy or treatment with an anti-DLL4 antibody and radiotherapy, such as IR, results in a synergistic effect. Combined therapies are "synergistic" if the outcome produced by the two therapies is greater than the sum of the outcomes achieved by each therapy separately. Outcomes that can be measured to determine whether two therapies are synergistic are those described herein, including in the Examples. For example, synergy may be evaluated in in vivo models using one or more criteria chosen from a delay in the time required for the tumor to regrow to the size it was prior to treatment, decreased tumor angiogenesis, increased tumor necrosis, increased tumor hypoxia, decreased metastasis (number of, or time to), decreased tumor volume, decreased tumor cell numbers, or increased survival time.

The methods of the invention are useful for treating cancers, tumors, and other neoplastic diseases.

A "cancer" in a mammal refers to any of a number of conditions caused by the abnormal, uncontrolled growth of cells. Cells capable of causing cancer, called "cancer cells", possess a number of characteristic properties such as uncontrolled proliferation, immortality, metastatic potential, rapid growth and proliferation rate, and certain typical morphological features. Often, cancer cells will be in the form of a tumor, but such cells may also exist alone within a mammal, or may be a non-tumorigenic cancer cell, such as a leukemia cell. Metastasis is the process by which cancer spreads from the place at which it first arose as a primary tumor to distant locations in the body. The cancer resulting from the spread of the primary tumor may be referred to as a metastasis, or as a metastatic cancer. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer (e.g., CA125, PAP, PSA, CEA, AFP, HCG, CA 19-9, CA 15-3, CA 27-29, LDH, NSE, and others), and detecting a genotype indicative of a cancer (e.g., TP53, ATM, etc.). However, a negative result in one or more of the above detection methods does not necessarily indicate the absence of cancer, e.g., a patient who has exhibited a complete response to a cancer treatment may still have a cancer, as evidenced by a subsequent relapse.

"Neoplasia," as used herein, refers to any aberrant growth of cells, tumors, malignant growths, warts, polyps, nonsolid tumors, cysts and other growths. A site of neoplasia can contain a variety of cell types, including but not limited, to neoplastic cells, vascular endothelia, or immune system cells, such as macrophages and leukocytes, etc.

Neoplastic diseases include, but are not limited to, melanoma, squamous cell carcinoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, and pancreatic cancer. Exemplary cancers in humans include a bladder tumor, breast tumor, prostate tumor, basal cell carcinoma, biliary tract cancer, bladder cancer, bone cancer, brain cancer, CNS cancer (e.g., glioma tumor), cervical cancer, vaginal cancer, choriocarcinoma, colon, rectum, anal canal cancer, connective tissue cancer, cancer of the digestive system; endometrial cancer, esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma, neuroblastoma, oral cavity cancer (e.g., lip, tongue, mouth, and pharynx); ovarian cancer; pancreatic cancer, retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas. Additional examples of tumors and neoplasias that can be treated are tumors and neoplasias of the types described elsewhere in the description and in the Examples.

In addition, embodiments include treatment of cancer, tumors, neoplasias, and malignant disorders in dogs, cats, and other pets. Such disorders include, but are not limited to, lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilm's tumor, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal tumor, testicular tumor, seminoma, Sertoli cell tumor, hemangiopericytoma, histiocytoma, chloroma (e.g., granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma, follicular lymphoma, intestinal lymphosarcoma, fibrosarcoma and pulmonary squamous cell carcinoma.

In some embodiments, a patient with a cancer, tumor, or neoplasia may have already failed one or more conventional cancer therapies, or conventional therapy may be contraindicated. In some of those embodiments, the patient has not been previously treated with radiation therapy, has not been treated with chemotherapy, has not been treated with an antibody therapy, has not been treated with hormone therapy, has not had the tumor or neoplasia surgically debulked, or has not had a combination of one or more of those therapies prior to the initial treatment with an anti-DLL4 antibody and radiation therapy.

In other embodiments, a patient with a cancer, tumor, or neoplasia may not have been previously treated for the cancer, tumor, or neoplasia. In these patients, treatment with an anti-DLL4 antibody, either alone or as part of a combination therapy with radiation therapy, may be in the initial treatment for the cancer, tumor, or neoplasia.

In those embodiments in which an anti-DLL4 antibody is administered to a patient with a cancer, tumor, or neoplasia in addition to treatment with radiation therapy, chemotherapy, antibody therapy, hormone therapy, or surgical debulking, the anti-DLL4 antibody improves the outcome that would otherwise have been obtained were the other treatment administered alone. An "improved outcome" may be judged by increased disease-free survival time, increased progression-free survival time, or increased overall survival time. "Disease free survival (DFS)" refers to the patient remaining alive, without return of the cancer, for a defined period of time such as about 1 year, about 2 years, about 3 years, about 4 years, about 5 years, about 10 years, etc., from initiation of treatment or from initial diagnosis. The events used in the analysis of DFS can include local, regional and distant recurrence of cancer, occurrence of secondary cancer, and death from any cause in patients without a prior event (e.g, breast cancer recurrence or second primary cancer). These criteria may likewise be used to determine whether a combination of therapies is synergistic. Additional criteria that show the effectiveness of combined treatment that includes an anti-DLL4 antibody and radiotherapy are set forth in the Examples.

In some embodiments, a reduction in the symptoms or severity of radiation necrosis of the nervous system, as described in Levin et al., Int J. Radiat Oncol Biol Phys (2011) 79(5):1487-95, may also be used as a measure of improved outcome following administration of an anti-DLL4 antibody in combination with IR.

Thus, in one aspect the invention provides methods of treating colorectal cancer by administering an anti-DLL4 antibody in combination with ionizing radiation (IR). In some embodiments, the first dose of anti-DLL4 antibody is administered after the initial dose of IR. In other embodiments, the first dose of anti-DLL4 antibody is administered before the IR. In still other embodiments, the first dose of anti-DLL4 antibody and the first dose of IR are administered on the same day. In some embodiments, an anti-DLL4 antibody is incorporated into a pre-existing protocol and it is used either in addition to, or in place of, treatment with an anti-angiogenic agent. Thus, in one embodiment, an anti-DLL4 antibody at a dose described herein is used in place of bevacizumab in the protocols described in Koukouakis et al., Clin. Cancer Res. (2009) 15(22):7069-76, in which the colorectal cancer is advanced, inoperable colorectal carcinoma and the treatment schedule comprises hypofractionated (3.4 Gy/fraction×15) split-course accelerated radiotherapy (biological dose equivalent of approximately 67 Gy), supported with amifostine, capecitabine (600 mg/m² daily, 5 days/week). In one embodiment the treatment results in an improved overall survival time or an improved overall survival rate or an improved progression-free survival time compared to the same protocol without addition of anti-DLL4 antibody.

In another aspect the invention provides methods of treating a pancreatic cancer by administering an anti-DLL4 antibody in combination with ionizing radiation (IR). In some embodiments, the first dose of anti-DLL4 antibody is administered after the initial dose of IR. In other embodiments, the first dose of anti-DLL4 antibody is administered before the IR. In still other embodiments, the first dose of anti-DLL4 antibody and the first dose of IR are administered on the same day. In some embodiments, an anti-DLL4 antibody is incorporated into a pre-existing protocol. Thus, in one embodiment the ionizing radiation and anti-DLL4 antibody are administered in combination with gemcitabine. In another embodiment, the anti-DLL4 antibody is used either in addition to, or in place of, treatment with an anti-angiogenic agent. For example, in one embodiment, an anti-DLL4 antibody at a dose and schedule described herein is added to the protocols described Picozzi et al., Annals Oncol. (2011) 22:348-54 in which the pancreatic cancer is a resected pancreatic adenocarcinoma and the treatment schedule comprises a 5.5 week cycle of fractionated (1.8 Gy/fraction×28) radiotherapy (biological dose equivalent of approximately 50 Gy) given five days/week for 5.5 weeks; 5-fluorouracil (5-FU) infused continuously for 38 consecutive days at 175 mg m²/day; cisplatin (30 mg/m² i.v.) weekly on the first day of each week of the 5.5 week cycle; interferon alfa-2b (3 million units) s.c. on days 1, 3, and 5 of each week of the 5.5 week cycle. Additional cycles of 5-FU may be added, with rests of two weeks in between. In one embodiment the treatment results in an improved overall survival time or an improved overall survival rate or an improved progression-free survival time compared to the same protocol without addition of anti-DLL4 antibody.

In still another aspect, the invention provides methods of treating a brain cancer such as glioblastoma multiforme by administering an anti-DLL4 antibody in combination with ionizing radiation (IR). In some embodiments, the first dose of anti-DLL4 antibody is administered after the initial dose of IR. In other embodiments, the first dose of anti-DLL4 antibody is administered before the IR. In still other embodiments, the first dose of anti-DLL4 antibody and the first dose of IR are administered on the same day. In some embodiments, an anti-DLL4 antibody is incorporated into a pre-existing protocol and it is used either in addition to, or in place of, treatment with an anti-angiogenic agent. Thus, in one embodiment, an anti-DLL4 antibody at a dose described herein is used in place of bevacizumab in the protocols described in Lai e al., J. Clin. Oncol. (2011) 29(2):142-48, in which the brain cancer is newly diagnosed glioblastoma multiforme and the treatment schedule comprises 10 mg/kg of biweekly antibody therapy administered i.v. and 75 mg/m² temozolomide (TMZ) orally during a radiotherapy phase (started 3 to 6 weeks following surgery) of 6 weeks comprising fractionated (2.0 Gy/fraction×30; approximately 60 Gy). Following completion of radiotherapy, antibody therapy continues every two weeks. After a 2-week minimum interval from last TMZ dose, patients are treated biweekly with antibody and TMZ every 4 weeks at 150 to 200 mg/m²/day for the first 5 days of each 28 day cycle until progression or for a maximum of 24 cycles, at which point non-progressing patients continue on antibody therapy every 2 weeks until progression. In another embodiment, bevacizumab is retained and anti-DLL4 antibody is added to the protocol at a dose and scheduled described herein. In still another embodiment, an anti-DLL4 antibody in combination with radiation is used at disease progression in recurrent glioblastoma using one of the radiotherapy protocols described in Beal et al., Radiat Oncol (2011) Jan 7:6:2. In one embodiment the treatment results in an improved overall survival time or an improved overall survival rate or an improved progression-free survival time compared to the same protocol without addition of anti-DLL4 antibody.

EXAMPLES

The following examples, including the experiments conducted and results achieved are provided for illustrative purposes only and are not to be construed as limiting upon the teachings herein.

The studies set forth in Example 1 to Example 6 utilized a human colorectal carcinoma xenograft system that endogenously expresses the Notch ligand, DLL4, to explore the interaction of global Notch blockade (via a GSI) or selective DLL4-Notch blockade, with ionizing radiation (IR) on tumor perfusion and growth.

Statistical Analysis

Unless otherwise noted, data are presented as the mean and standard error. Statistical significance was determined using one-way analysis of variance with a Dunnett's post test in the GraphPad Prism program version 4.0 (GraphPad Software, USA); a value of $p<0.05$ was considered to be statistically significant.

Example 1

Notch Signaling Inhibitors and Cell Lines

Notch Signaling Inhibitors

The production of several anti-DLL4 antibodies is described in detail in US2010/0196385, "Targeted Binding Agents Directed to DLL4 and Uses Thereof" by Vehe Bedian, David Jenkins, and Ian Foltz, which also published as WO 2010/032060. Each of those publications is incorporated by reference in its entirety. One of those anti-DLL4 antibodies, the human antibody 2A5, was used in the examples that follow (where it is referred to as "DLL4 mAb"), but its use is exemplary only.

Dibenzazepine (DBZ) is a γ-secretase inhibitor that can be used to block essentially all Notch signaling. However, γ-secretases have a broad range of potential substrates in addition to Notch receptors (Fortini M E, Nat Rev Mol Cell Biol. 2002, 3(9):673-84).

Cell Lines

To identify and validate a model colorectal carcinoma cell line for intact Notch signaling, Oncomine was used to screen the Wooster cell line panel for DLL4 expression (data not shown). DLL4 expression was predicted in several colorectal adenocarcinoma cell lines, including LS174T, HCT-15, and COLO 201. The LS174T, LS180 (the cell line that LS174T was derived from), COLO 205 (a cell line derived from the same patient as COLO 201), HCT-15 human colonic adenocarcinoma cell lines and FaDu human hypopharyngeal squamous cell carcinoma cell line were purchased from the American Type Culture Collection (CL-188; CL-187; CCL-222; CCL-225; HTB-43, respectively). Cell lines were cultured in Dulbeco's Modified Eagle Medium containing 4.5 g/L glucose (Invitrogen) supplemented with 10% fetal bovine serum (Lonza), and penicillin-streptomycin (Invitrogen) (10% DMEM), and maintained in an incubator with 5% CO2, at 3° C. They were passaged when they reached approximately 80% confluency, and they were regularly tested to ensure the absence of Mycoplasma contamination (MYCOALERT™, Lanza). Cell morphology was regularly checked to ensure the absence of cross-contamination of cell lines.

Example 2

DLL4 is a Major Notch Signaling Ligand

The colorectal adenocarcinoma lines COLO 205, LS174T, LS180, and HCT-15 were analyzed for expression of DLL4 and other Notch receptors by western blotting. Cells were rinsed once with phosphate-buffered saline, then lysed in ice cold RIPA lysis buffer (50 mM Tris-HCl pH 7.4, 150 mM NaCl, 1 mM EDTA, 1% NP-40, 0.5% sodium deoxycholate, 0.1% sodium dodecyl sulfate) containing COMPLETE™ Protease Inhibitor Cocktail (Roche), and phosphatase inhibitors (1 mM NaF, 2.5 mM sodium pyrophosphate, 1 mM sodium orthovanadate), ultrasonicated for 1 min, and lysates clarified by centrifugation at 16,500 RPM at 4° C. for 10 min. Protein lysate concentration was determined by the Bradford protein assay (Bio-Rad), and 25-30 IIg of lysate denatured in SDS sample buffer (58 mM Tris-HCl, pH 6.8, 1.71% SDS, 0.83% Pmercaptoethanol, glycerol 6%, 0.002% bromophenol blue) at 100° C. for 5 min and proteins electrophoretically resolved on NOVEX™ 4-12% Tris-glycine gels (Invitrogen). Proteins were wet transferred onto polyvinylidene fluoride membrane (Millipore), the membrane blocked in 5% non-fat dry milk power in TBST (10 mM Tris-Base, 150 mM NaCl, 0.05% TWEEN™ 20 (polysorbate 20); pH 7.4) for 1 hr at room temperature, then incubated with primary antibody in 5% milk/TBST overnight at 4° C. with gentle agitation. Three washes of TBST were performed for 10 min each, followed by corresponding secondary antibody conjugated to horseradish-peroxidase in 5% milk/TBST at room temperature for 1 hr, followed by three 10 min TBST washes. Western blots were visualized with ECL PLUS™ solution (Amersham) followed by exposure to X-ray film (FujiFilm). The primary anti-DLL4, anti-Jagged 1, anti-Notch1 ICD, anti-Notch1, 2 and 3 rabbit polyclonal antibodies were used at 1:1000 dilution (Cell Signaling Technology); anti-Notch4 rabbit polyclonal was used at 1:200 dilution and anti-β-actin goat polyclonal was used at 1:6000 dilution (Santa Cruz Biotechnology).

Figure 1B:
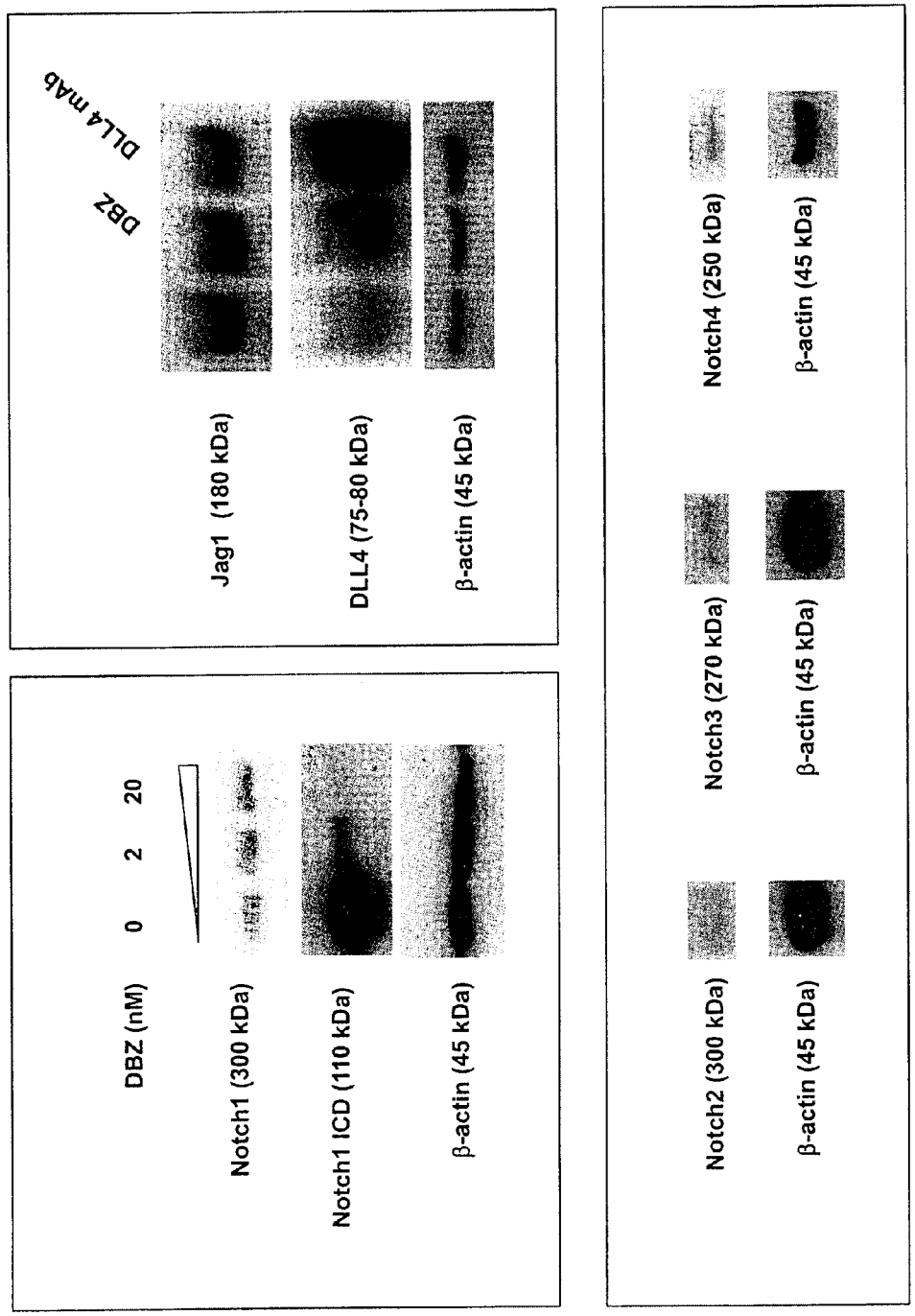
FIG. 1B depicts immunoblots of LS174T cells treated with increasing amounts of DBZ then blotted for Notch1 and N1ICD (left panel); cells treated with DBZ or DLL4 mAb then blotted for Jag1 or DLL4 (right panel); and untreated LS174T cells blotted for Notch 2, 3, and 4 receptors (bottom panel).

DLL4 was highly expressed in COLO 205, LS174T and LS180, and expressed at a low level in HCT-15 (FIG. 1A). LS174T cells also express all four Notch receptors (FIG. 1B, upper left and lower panels). When LS174T cells were incubated with DMSO or DBZ (2 or 20 nM) and then immunoblotted for Notch1 and Notch 1ICD; the gamma-secretase inhibitor DBZ inhibited the production of N1ICD in a dose-dependent manner (FIG. 1B, left panel). Equal loading was confirmed with immunoblotting for β-actin. Treatment of LS174T cells with DBZ (20 nM) or DLL4 mAb (1 µg/mL) overnight led to upregulation of DLL4 expression (FIG. 1B, right panel). DBZ and DLL4 mAb caused an increase in DLL4 protein levels, suggesting that Notch signaling may negatively regulate DLL4 expression (FIG. 1B, upper right panel). LS174T cells also express Jagged 1, however in contrast to DLL4, the expression of this Notch ligand is not affected by DBZ or DLL4 mAb (FIG. 1B, upper right panel).

To generate a stable Notch-reporter cell line, LS174T cells were infected with a lentivirus harboring a minimal promoter with multiple Notch RBP-jK response elements driving expression of the firefly luciferase gene (SA Biosciences). Stable pooled lines were established by puromycin selection (2 µg/ml). The resulting LS174T Notch-luc cells were then assessed for luciferase activity in response to recombinant DLL4 in the presence or absence of inhibitors. Briefly, cell lines stably expressing a Notch-luciferase reporter were seeded onto 24-well dishes precoated with BSA or recombinant DLL4 (R&D systems) as previously described (Harrington et al., Microvasc Res. 2008, 75(2):144-54) in 10% DMEM containing vehicle (DMSO), mouse isotype IgG1 (1 µg/ml; R&D Systems), DBZ (20 nM), or DLL4 mAb (1 µg/ml) for 24 hr. To assess Notch-luciferase activity, D-luciferin (150 µg/ml; Gold BioTechnology) was added to the medium for 2 min, luminescent readings captured with a Xenogen IVIS™ 200 (Caliper Life Sciences), and analyzed with Living Image 3.0 software (Caliper Life Sciences).

As shown in FIG. 1C, basal level and DLL4-induced Notch activity was abrogated by DBZ and by DLL4 mAb. The bar graph displays the fold change in Notch luciferase activity (DLL4-coated plates normalized to BSA-coated plates), with standard error indicated. The "*" denotes a significant difference (p<0.01) compared to DMSO control. The bottom panel of FIG. 1c shows a 'heat map' of Notch luciferase activity. DLL4 mAb inhibited Notch activity in an equivalent manner to DBZ, indicating that DLL4 is a major Notch signaling ligand in these cells.

Example 3

Notch Blockade does not Affect Proliferation or Apoptosis

Figure 2A:
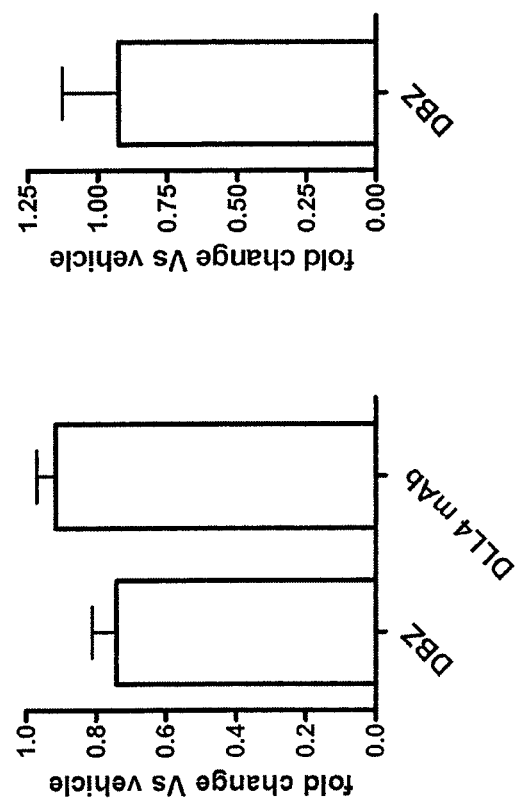
FIG. 2A depicts the fold change versus vehicle in total cell numbers of LS174T cells incubated with DBZ or DLL4 mAb after 5 days of culture. Standard error bars are shown.

Gamma-secretase inhibitors (GSis) have been reported to decrease proliferation of certain tumor cells and to promote apoptosis (Suwanjunee et al., Anticancer Drugs 2008, 19(5):477-86; Efferson et al., Cancer Res. 2010, 70(6):2476-84; Fan X et al., Stem Cells 2009, 28(1):5-16; Rasul et al., Br J Cancer 2009, 100(12):1879-88; Curry et al., Oncogene 2005, 24(42):6333-44). LS174T cells were incubated in triplicates with vehicle, DBZ (20 nM) or DLL4 mAb (1 µg/mL), total number of cells counted after 5 days with a NUCLEOCOUNTER™ NC-100 (ChemoMetec), and divided by the total number of cells counted in the vehicle treated samples to obtain the fold change. The mean and standard errors were plotted. In this case, DBZ decreased proliferation by approximately 25% relative to untreated LS174T cells, however this was not statistically significant (p=0.065) (FIG. 2A). Likewise, DLL4 mAb did not cause a statistically significant reduction in proliferation (FIG. 2A).

Figure 2B:
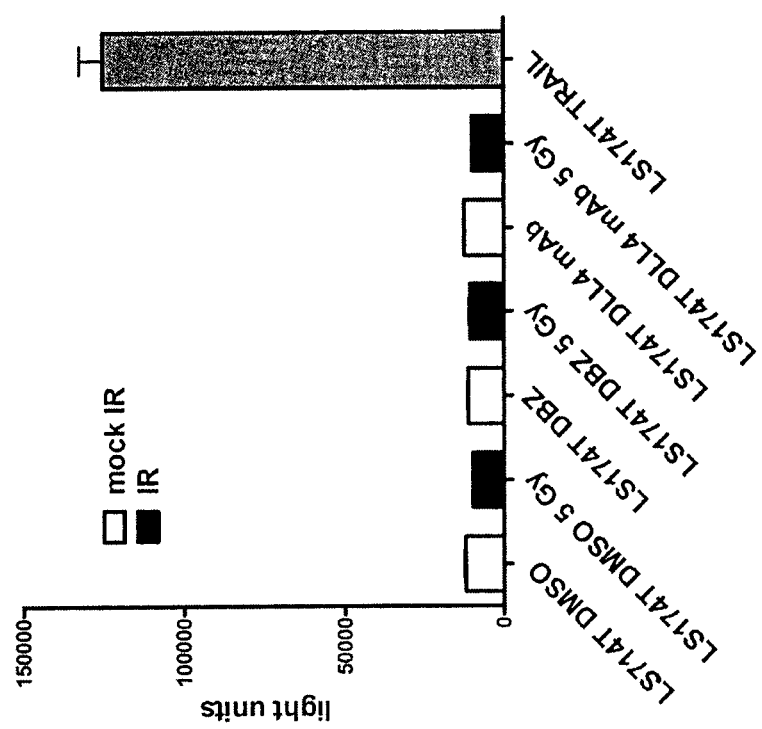
FIG. 2B depicts light units obtained from LS174T cells treated with vehicle, DBZ, or DLL4 mAb, in combination with either mock irradiation or a 5 Gy dose of IR. LS174T cells incubated with 50 nM recombinant TRAIL (R&D Systems) for 2 hrs provide a positive control.

To assay whether apoptosis was induced in the cultures, LS174T cells were seeded in triplicates in white-walled 96 wells with vehicle, DBZ (20 nM or DLL4 mAb (1 µg/mL), and either mock irradiated or irradiated with a 5 Gy dose of IR. As a positive control for apoptosis, LS174T cells were incubated with 50 nM recombinant TRAIL (R&D Systems) for 2 hrs. Apoptosis was quantified using the CAPASE-GLO™ 3/7 Assay system (Promega) as per the manufacturer's instructions. While TRAIL treatment led to a large increase in apoptosis, Notch blockade with DBZ and DLL4 mAb, whether alone or in combination with IR treatment, did not result in significantly increased apoptosis in vitro (FIG. 2B).

Example 4

Notch Signaling is Inhibited by Ionizing Radiation but Notch Blockade does not Contribute to Radiosensitization GSIs have been reported to radiosensitize glioma stem cells (Wang et al. Stem Cells 2009, 28(1):17-28). Accordingly, Notch inhibition with DBZ or DLL4 blockade was tested for radiosensitization of LS174T cells in vitro. For the clonogenic survival assays, cells were counted and seeded in triplicates at low density in 10% DMEM containing vehicle (DMSO), DBZ (20 nM), or DLL4 mAb (1 µg/mL), then mock irradiated or irradiated with a 2, 4 or 6 Gy dose of IR using an IBL634 cesium irradiator (CIS Biointernational) at a dose rate of 0.66 Gy/min. Colonies were stained with crystal violet and counted 14 to 21 days later. The surviving fraction was plotted and the data modeled to the linear quadratic equation as previously described (Liu et al. Radiother Oncol. 2008, 88(2):258-68).

Figure 3A:
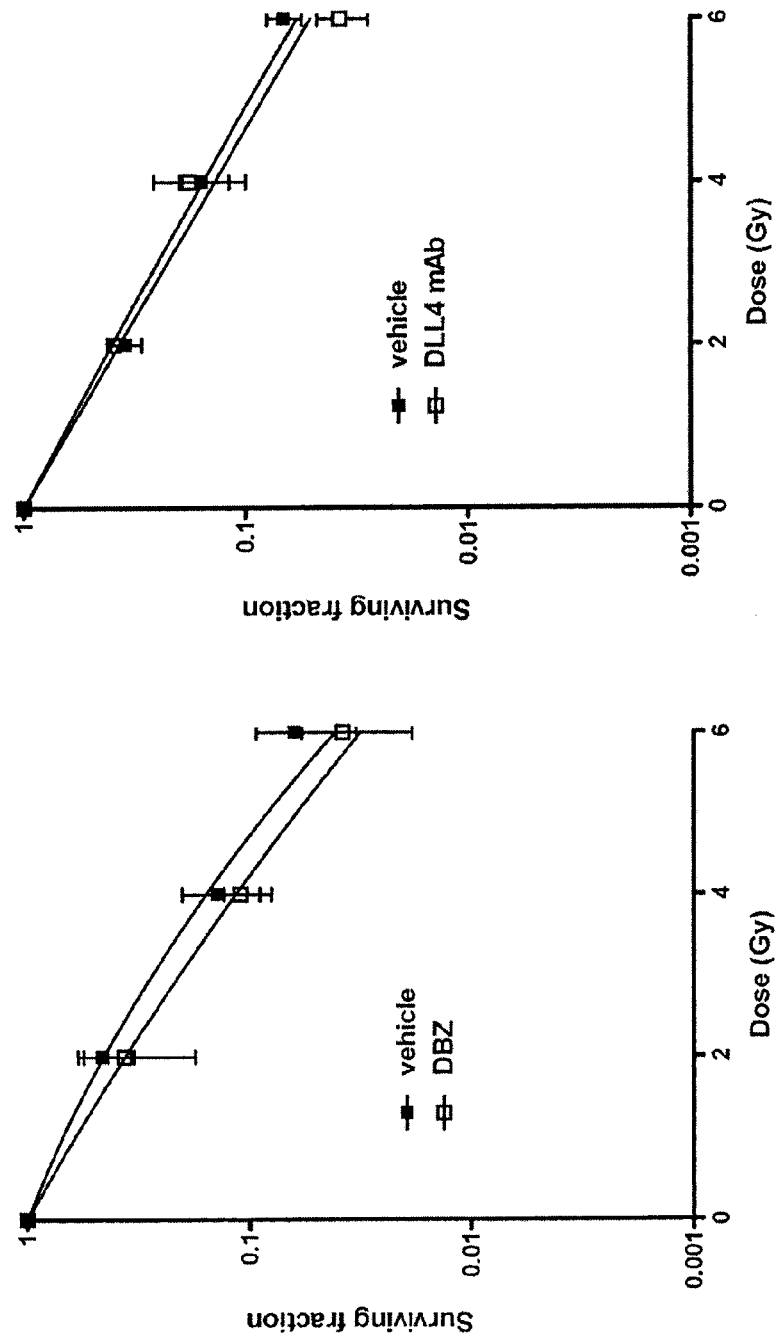
FIG. 3A depicts the surviving fraction of LS174T cells following incubation with vehicle, DBZ (left panel), or DLL4 mAb (right panel), when cells are mock irradiated or irradiated with a 2, 4 or 6 Gy dose of IR. The surviving fraction is plotted and the data modeled to the linear-quadratic equation, with means and standard error bars shown.
Figure 3B:
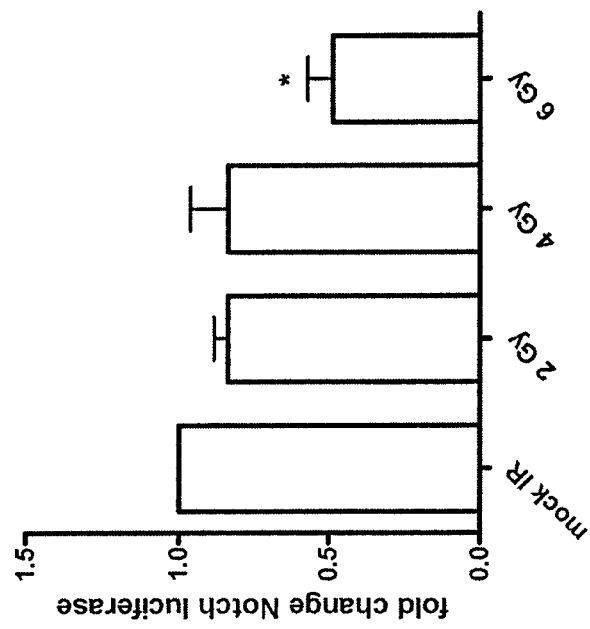
FIG. 3B depicts the fold change in luciferase activity 24 hours after LS174T Notch-luc cells were mock irradiated or irradiated with a 2, 4 or 6 Gy dose of IR. "*" denotes $p<0.05$.

Notch inhibition with DBZ or DLL4 mAb blockade did not significantly radiosensitize LS174T cells in vitro (FIG. 3A). Means and standard error bars are shown. However, compared to the mock IR control, there was a significant reduction in Notch activity following a 6 Gy dose of IR measured 24 hrs later ("*" denotes p<0.05) (FIG. 3B). The reduction in Notch activity was not due to a reduction in cell number (data not shown). This dose of IR also led to a reduction in DLL4 and N1ICD levels as assessed by western blotting (data not shown), which may partly explain the resulting suppression of Notch activity by IR. Thus, although IR can downregulate Notch signaling, this pathway does not play a relevant role in clonogenic survival following IR in the context of LS174T colorectal carcinoma cells.

Example 5

Global Notch Inhibition and DLL4 Blockade Synergize with IR

This series of experiments examined the ability of a global notch inhibitor or DLL4 to synergize with IR in tumor xenograft models. All experiments involving mice were performed according to University of Oxford institutional guidelines and within the limits of the Project License issued by the Home Office, United Kingdom, as well as in accordance with the guidelines for the welfare and use of animals in cancer research (Workman et al., *Br J Cancer.* 2010; 102(11):1555-77). The LS174T Notch-luciferase cell line was grown as subcutaneous xenografts in BALB/C Nude mice. Previously, others have shown that LS174T xenografts have a heterogeneous tumor vasculature architecture that closely resembles patient colon carcinoma samples (E I Emir et al. Cancer Res. 2007, 67(24):11896-905; Folarin et al., Microvasc Res. 2010, 80(1):89-98), making this a relevant preclinical model to investigate anti-angiogenic therapies. Notch inhibition can promote non-functional angiogenesis which could theoretically decrease the efficacy of IR if given beforehand due to increased tumor hypoxia. Similarly, DLL4 blockade is known to increase tumor hypoxia, which could antagonize the effects of IR. Accordingly, for this initial experiment, both DBZ and DLL4 mAb treatments were sequenced to follow IR for the combined groups.

In brief, 10×10$^6$ LS174T Notch-luc cells were mixed with Matrigel in a 1:1 ratio, and injected subcutaneously into the right flank of six to seven week old female BALB/C nude mice (Harlan or Charles River). Tumor volume was determined by the modified ellipse formula (volume=length× width$^2$÷2). When the xenograft tumors reached approximately 100 mm$^3$ volume, the mice were randomized into vehicle or experimental arms. DBZ was dissolved in 0.5% Methocel and 0.1% Tween-80, then injected i.p. (8.1 uM/kg) every three days for a total of five doses beginning on day 1, or 30 min after IR on day 1. Anti-DLL4 blocking monoclonal Ab (DLL4 mAb) was injected i.p (5 mg/kg) beginning on day 1, or 30 min after IR on day 1, and injections continued twice per week. For irradiation, mice were anaesthetized, placed in a specialized brass jig to expose the tumor while shielding the remainder of the body, and the tumor irradiated with X-rays produced by a Gulmay RS320 (Gulmay Medical Ltd.) to a dose of 5 Gy. In the "DBZ Experiment," the groups were vehicle, DBZ, 5 Gy IR, and 5 Gy IR with DBZ. In the "DLL4 mAb Experiment," the groups were vehicle, DLL4 mAb, 5 Gy IR and 5 Gy IR with DLL4 mAb.

Notch Activity In Vivo

Three mice from each arm had in vivo luciferase imaging performed at day 1 (prior to treatment) and day 2 (post-treatment) to assess Notch reporter activity in the xenograft tumors. In this assay, mice were anaesthetized with 2% isofluorane, and placed inside the IVIS 200 (Caliper Life Sciences) chamber and anesthesia maintained with 2% isofluorane. D-luciferin was given by i.p. injection (150 mg/kg; Gold BioTechnology) 5 min prior to imaging. For image acquisition, parameters were f/stop 1, bin Med, exposure time 1 min. Signal intensity was quantified as the total photons/sec within a region of interest positioned over the tumor site. Results were analyzed using Living Image 3.0 software (Caliper Life Sciences).

Figure 4:
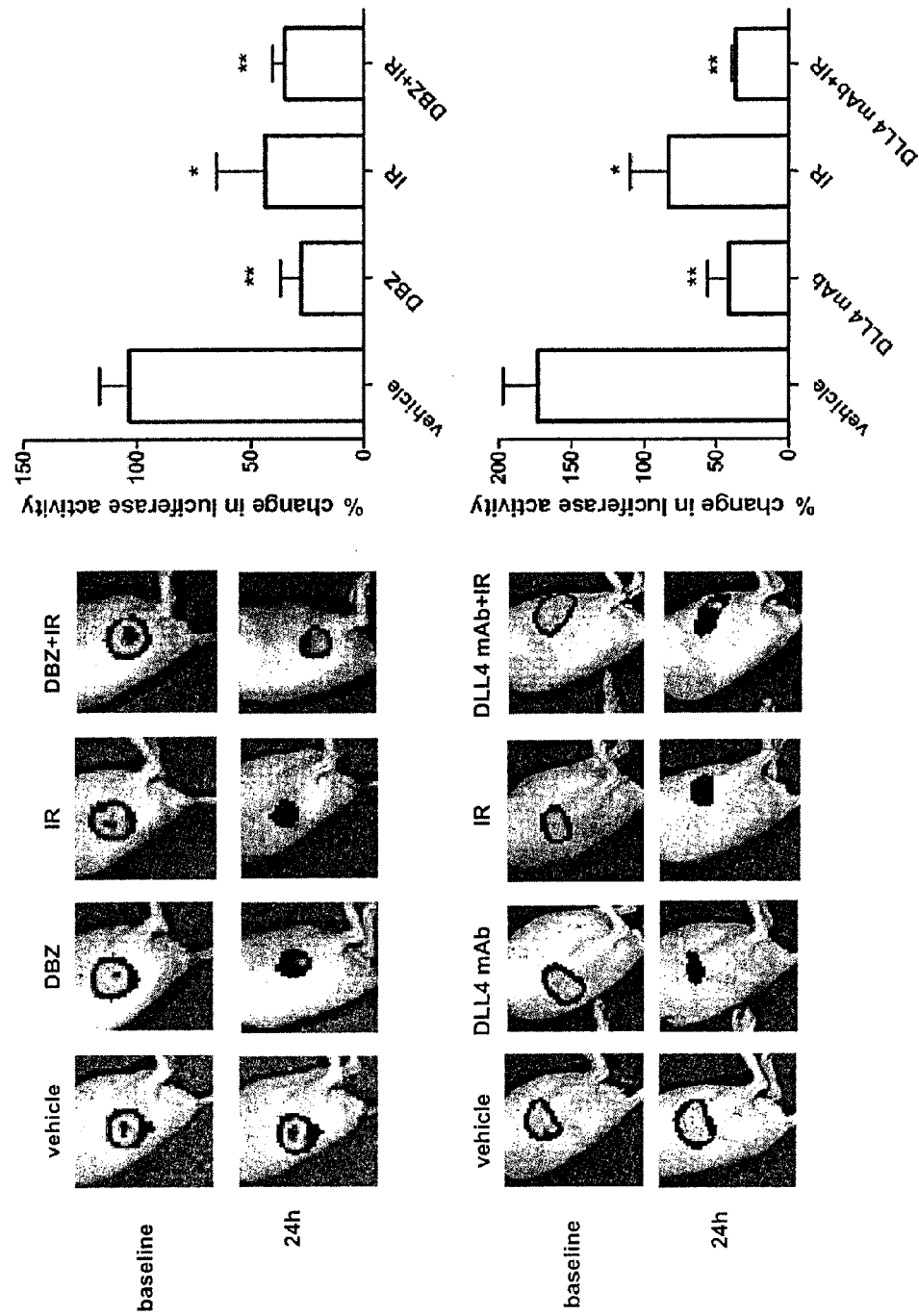
FIG. 4 presents tumor bioluminescence (left images) and the percent change in luciferase activity (bar graphs). Tumor bioluminescence was measured before and 24 hr after vehicle, DBZ, 5 Gy IR, or 5 Gy IR and DBZ treatment (top image panel and bar graph) and before and 24 hr after vehicle, DLL4 mAb, 5 Gy IR, or 5 Gy IR and DLL4 mAb (bottom image panel and bar graph). The 'heat map' overlying the tumors in the image panels displays relative Notch activity. "*" denotes $p<0.05$; "**" denotes $p<0.01$.

FIG. 4 presents the images and the graphic data for this experiment. The top left panel shows baseline and 24 hr after vehicle, DBZ, 5 Gy IR, or 5 Gy IR and DBZ treatment. The bottom left panel shows baseline and 24 hr after vehicle, DLL4 mAb, 5 Gy IR, or 5 Gy IR and DLL4 mAb treatment. In each panel, the 'heat map' overlying the tumors displays relative Notch activity, which is reduced following the treatments. The average fold change in Notch luciferase activity, generated from 3 to 5 mice per group, is shown in bar graph form (right panels). Vehicle treated mice showed no change in Notch luciferase activity. DBZ or DBZ and IR treatment inhibited activity to 28±9% and 35±5% of baseline, respectively, which were both significant compared to vehicle ($p<0.01$). IR alone also significantly reduced Notch reporter luciferase in the tumors to 44±21% of baseline luciferase ($p<0.05$). To assess a more selective inhibitor of Notch signaling, the xenograft experiment was repeated with DLL4 mAb. In agreement with the in vitro data, DLL4 mAb or DLL4 mAb and IR treatment inhibited Notch luciferase activity in vivo to 41±14% and 36±3% of baseline, respectively.

Tumor Growth Delay

Figure 5:
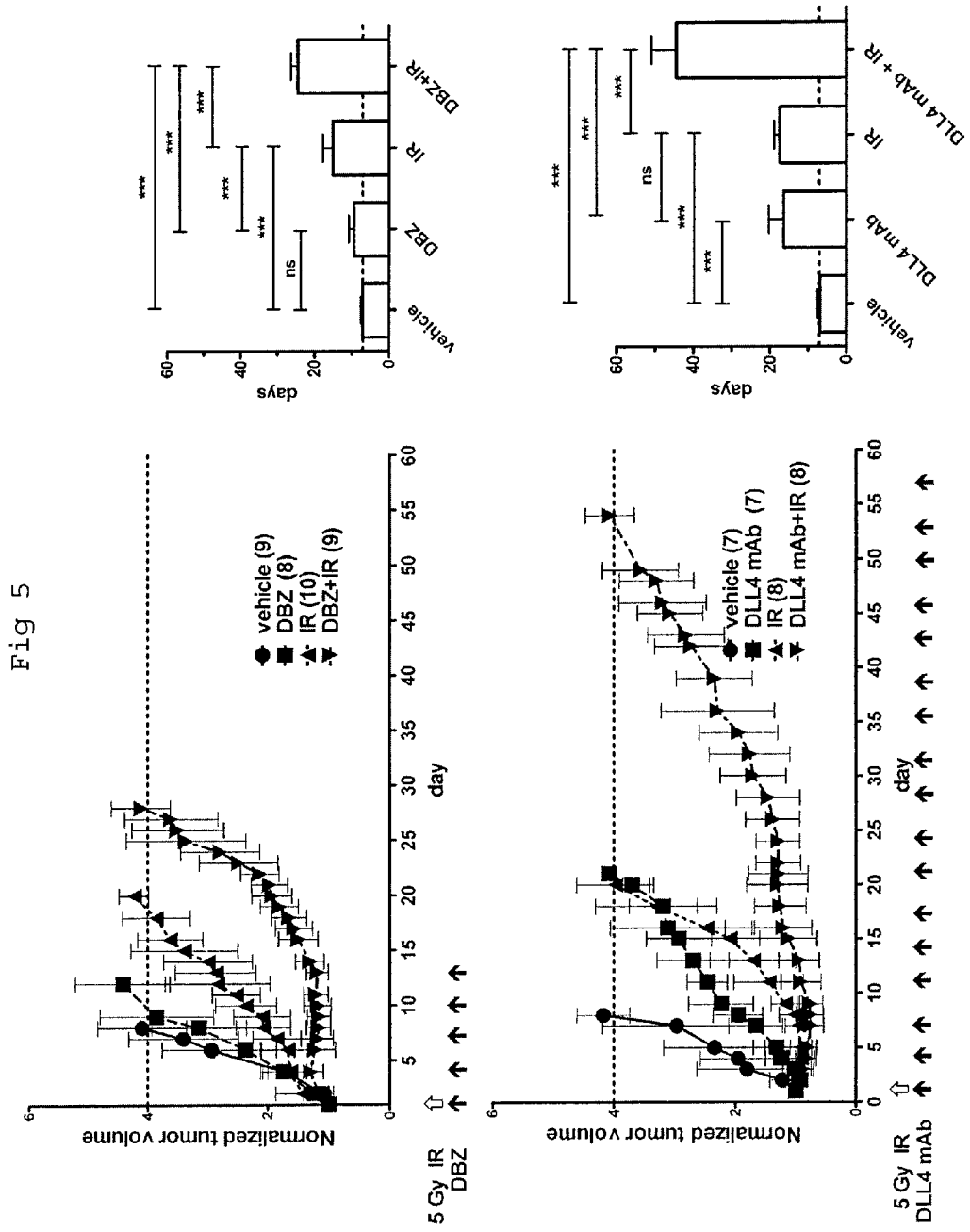
FIG. 5 depicts the effect of therapy on tumor volume. The two left graphs are survival graphs showing the treatment course, as indicated by the arrow heads on the X-axis, versus the normalized tumor volume on the Y-axis. The upper survival graph compares treatment with vehicle (circle, N=7), DBZ (square, N=8), 5 Gy IR (triangle, N=10), and 5 Gy IR plus DBZ (inverted triangle, N=9). The lower survival graph compares vehicle (circle, N=7), DLL4 mAb (square, N=7), 5 Gy IR (triangle, N=8), and 5 Gy IR plus DLL4 mAb (inverted triangle, N=8). The bar graphs on the right depict the average time for tumors to reach four times the starting volume (RTV4) along with standard deviations. The dotted line indicates RTV4 for the vehicle-treated tumors; the extent of the respective bars above this line corresponds to tumor growth delay. "***" denotes a statistically significant difference ($p<0.001$); "ns" denotes a non-significant difference.

FIG. 5 presents survival graphs in which tumor volume is shown relative to the treatment course in days. Mice bearing subcutaneous LS174T Notch-luc xenografts were randomized to vehicle or treatment groups when tumor volumes were approximately 100 mm$^3$ (i.e., day 1), and tumor volumes determined by caliper measurement every 1-3 days. In the "DBZ Experiment" shown in the upper graphs, the groups were vehicle, DBZ, 5 Gy IR, or 5 Gy IR with DBZ. DBZ was administered on day 1, and then every three days for a total of five doses. In the "DLL4 mAb Experiment" shown in the lower graphs, the groups were vehicle, DLL4 mAb, 5 Gy IR or 5 Gy IR with DLL4 mAb. DLL4 mAb was given twice per week for the duration of the experiment. In the survival graphs shown in FIG. 5, the timing of IR and Notch inhibitor treatment is depicted by arrowheads on the time axis. Tumor volumes were normalized relative to day 1 tumor volumes, and the mean normalized tumor volumes and standard deviation plotted on the survival curves. Mice were sacrificed when their normalized tumor volumes reached four times the starting volume (RTV4), shown as a dotted line on each survival curve. The total number of mice in each group is shown in the legend within parentheses. The average time for tumors to reach RTV4 and standard deviation for each group is shown in the bar graphs. The dotted line indicates RTV4 for the vehicle-treated tumors; the extent of the respective bars above this line corresponds to tumor growth delay.

The numerical results for the DBZ experiment are presented in Table 1.

TABLE 1

| Group | RTV4 (days) | Tumor Growth Delay (days) |
|---|---|---|
| Vehicle | 7.1 ± 0.6 | |
| DBZ | 9.5 ± 1.4 | 1.6 ± 1.4 |
| IR | 15.1 ± 2.7 | 8 ± 2.8 |
| DBZ + IR | 24.4 ± 1.8 | 17.3 ± 1.9 |

In the DBZ experiment, the average time for tumor volumes in the vehicle group to reach RTV4 was 7.1±0.6 days, and for mice treated with DBZ, it was 9.5±1.4 days, a difference that was not statistically significant. The IR group took an average of 15.1±2.7 days to reach RTV4, with a tumor growth delay of 8±2.8 days, which was significantly longer than either vehicle or DBZ ($p<0.001$). The combined DBZ and IR treatment reached RTV4 in 24.4±1.8 days (significantly longer than either of the treatments given solely; $p<0.001$), producing a tumor growth delay of 17.3±1.9 days. The combined result was more than additive for the individual treatments in delaying tumor growth.

The numerical results for the DLL4 mAb experiment are presented in Table 2.

TABLE 2

| Group | RTV4 (days) | Tumor Growth Delay (days) |
|---|---|---|
| Vehicle | 6.8 ± 0.2 | |
| DLL4 mAb | 16.4 ± 1.4 | 9.6 ± 1.4 |
| IR | 17.3 ± 0.5 | 10.5 ± 0.5 |
| DLL4 mAb + IR | 44.3 ± 2.3 | 37.5 ± 2.3 |

In the DLL4 mAb experiment, tumors in the vehicle group reached RTV4 in 6.8±0.2 days. As a single agent treatment, DLL4 blockade reached RTV4 at 16.4±1.4 days; resulting in a growth delay of 9.6±1.4 days. Thus DLL4 blockade was more effective than DBZ in prolonging tumor growth delay. In fact, since IR treatment in this experiment reached RTV4 at 17.38±0.5 days, resulting in a tumor growth delay of 10.6±0.5 days, there was no statistically significant difference between the DLL4 and IR treatments in growth delay. The combined treatment reached RTV4 in 44.3±2.3 days, yielding a profound tumor growth delay of 37.5±2.3 days ($p<0.001$). This was more than double the tumor growth delay of 17.3±1.9 days observed with DBZ and IR combination treatment. Therefore, although both a global Notch inhibitor and a selective DLL4 inhibitor were synergistic when combined with IR, the DLL4 inhibitor produced a superior effect.

Tumor Perfusion

To monitor treatment effects on tumor perfusion in real time, three mice bearing LS174T Notch-luc xenografts from each study arm had microbubble contrast ultrasound imaging performed at day 1 (prior to treatment when tumors were approximately 100 mm$^3$), or at day 5 or 7 post-treatment. Tumor perfusion was evaluated with the Vevo 770 Micro-Ultrasound platform (Visualsonics) with the RMV-704 probe by image enhancement using contrast microbubbles (Vevo MICROMARKER™ Contrast Agent Kit), according to the manufacturer's instructions. For each study, a fresh vial was prepared with saline. Microbubbles ($1\times10^8$) were injected as a bolus in a volume of 50 μL via a 27-gauge hypodermic needle into a lateral tail vein under direct visualization. Before administration of microbubbles, a baseline image sequence was acquired in contrast mode at a frequency of 40 MHz. This was followed by a dynamic sequence commenced just before microbubble injection for 40 sec, acquired in a total of 550 frames. The region of interest (ROI) was delineated, acquired images were processed, taking into account baseline intrinsic contrast intensity, and quantitative perfusion as well. Contrast kinetics analysis was performed using the intrinsic Vevo 770 software (v.2.23) to assess the slope and magnitude of the microbubble influx. Relative tumor blood flow, calculated from the ROI, was normalized to the untreated (control) group.

Figure 6:
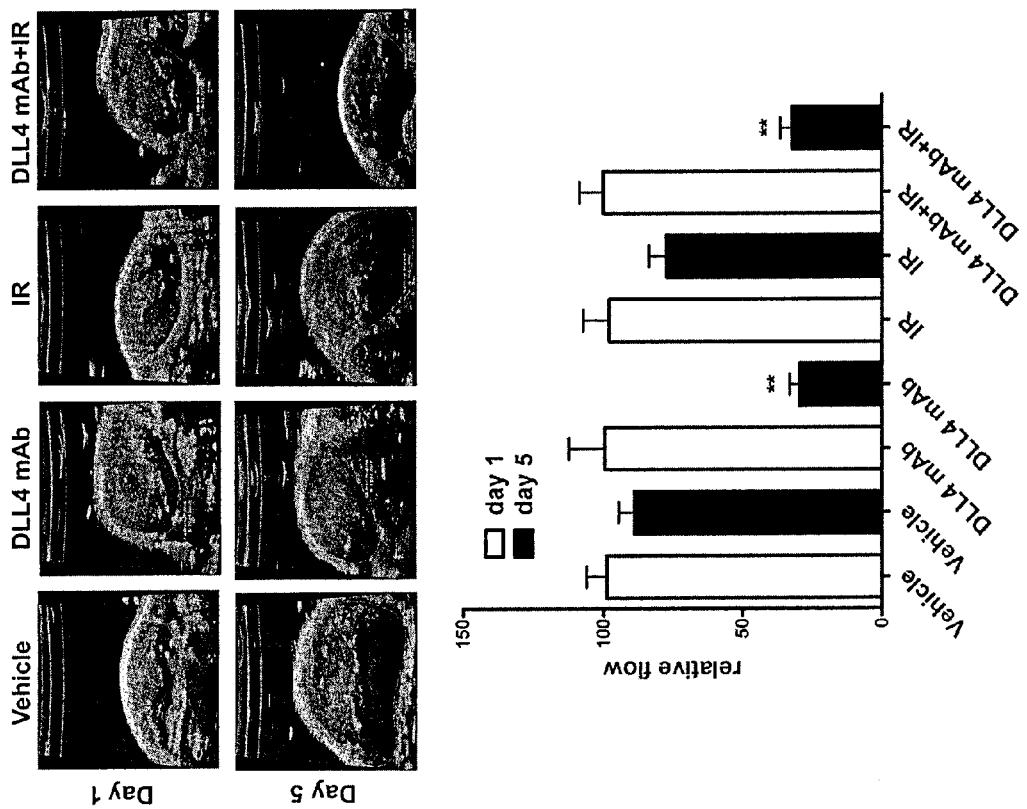
FIG. 6 shows microbubble contrast ultrasound analysis of tumor perfusion. The top panel presents images taken on day 1 and day 5. The bar graph presents the relative tumor blood flow values normalized to the vehicle group. The mean and standard error was derived from three independent experiments. "**" denotes $p<0.01$ relative to vehicle.
Figure 9A:
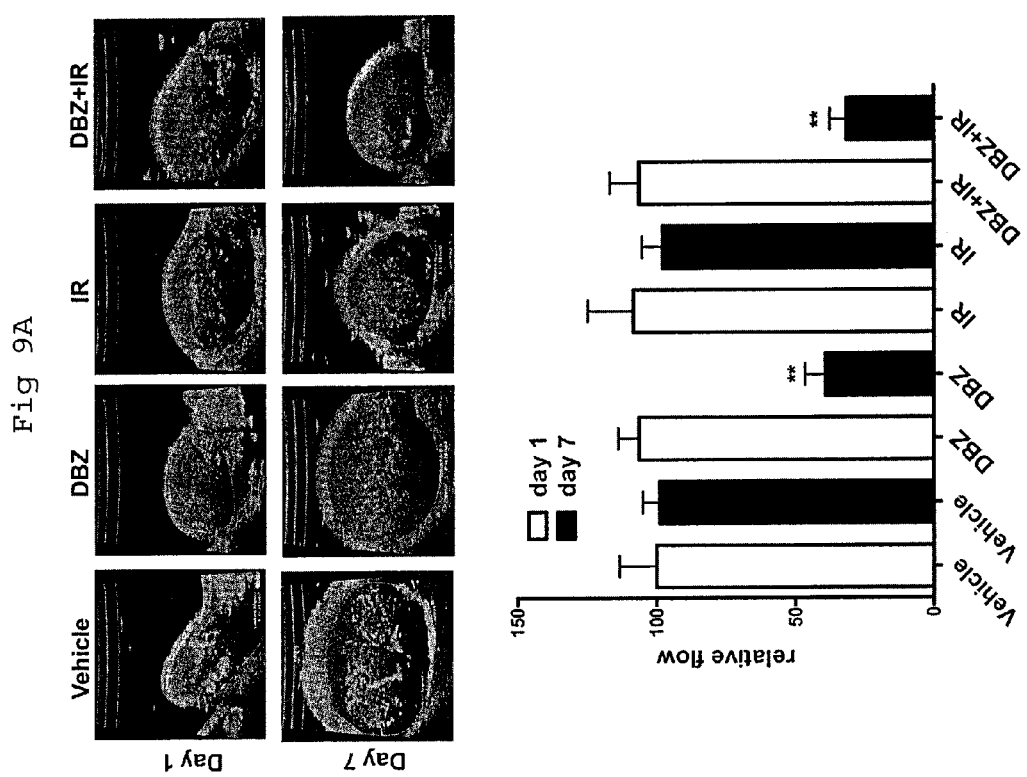
FIG. 9A shows microbubble contrast ultrasound analysis of tumor perfusion. The top panel presents images taken on day 1 and day 7. The bar graph presents the relative tumor blood flow values normalized to the vehicle group. The mean and standard error were derived from three independent experiments. "**" denotes $p<0.01$ relative to vehicle.
Figure 9B:
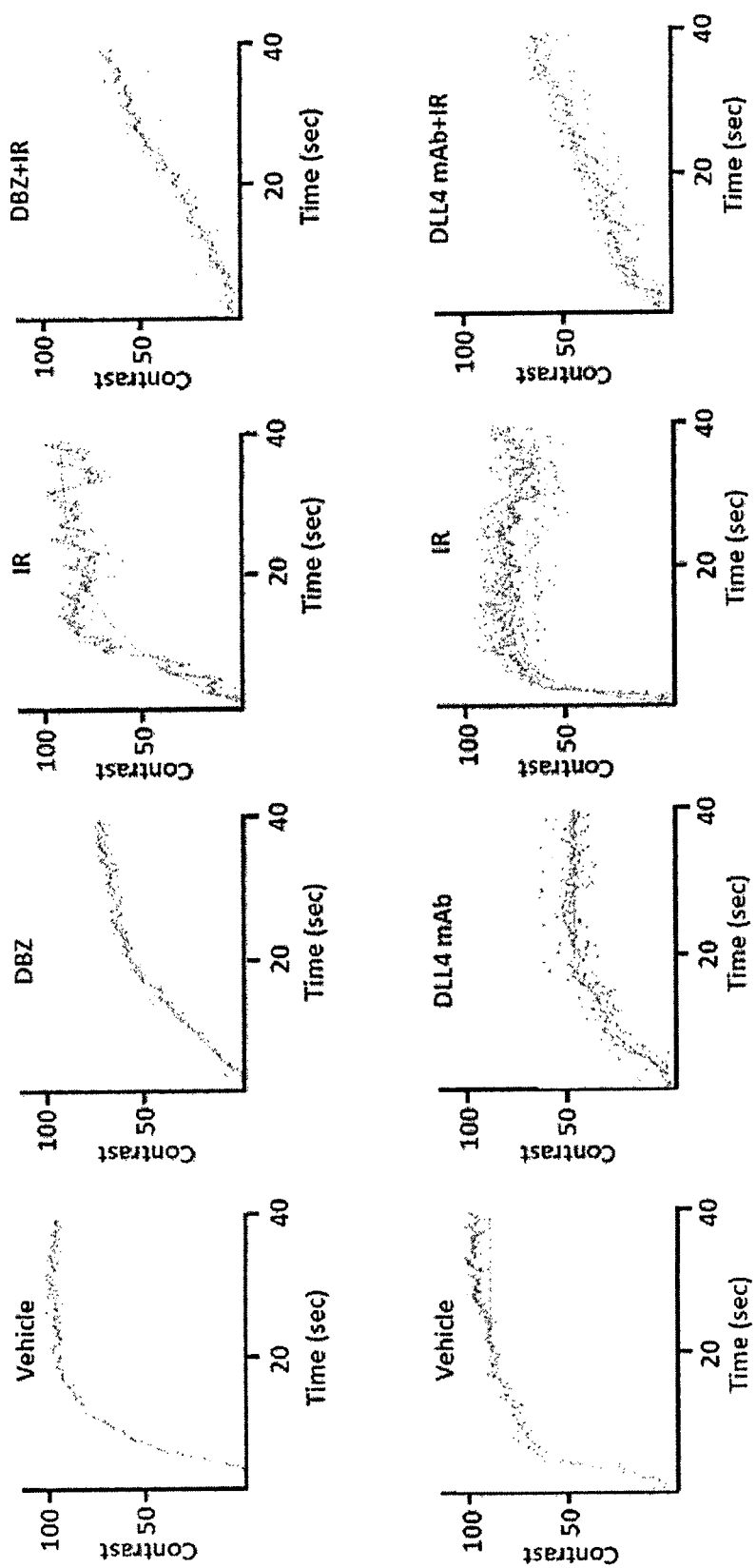
FIG. 9B shows a contrast kinetics (total contrast signal and rate) analysis for the effect of DBZ or DLL4 mAb either alone or in combination with IR.
Figure 9C:
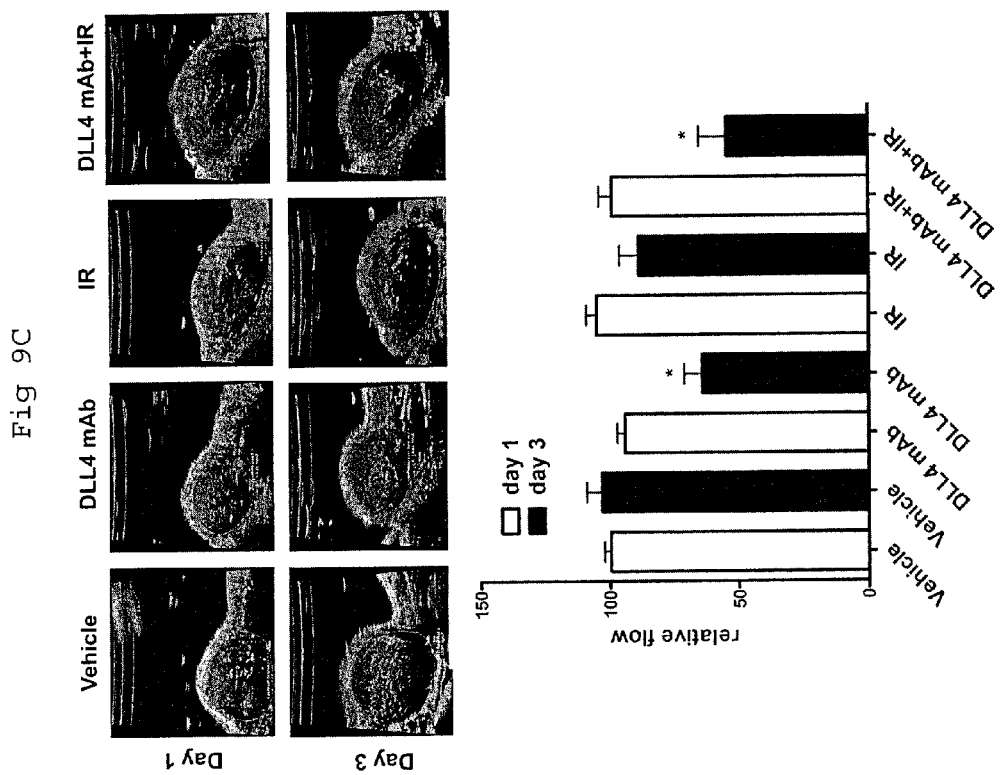
FIG. 9C shows microbubble contrast ultrasound analysis of tumor perfusion. The top panel presents images taken on day 1 and day 3. The bar graph presents the relative tumor blood flow values normalized to the vehicle group. The mean and standard error were derived from three independent experiments. "*" denotes p<0.05 relative to vehicle.

FIG. 6, FIG. 9A, and FIG. 9C show perfusion as depicted by microbubble contrast agent (green signal) that is proportional to the number of microbubbles within the region of interest (ROI) outlining each tumor. For each set of microbubble images, relative tumor blood flow values were normalized to the vehicle (control) group, and the mean and standard error derived from three independent experiments is shown in the bar graphs. Results for day 1 and day 7 of the DBZ experiment are shown in FIG. 9A. For the DLL4 mAb experiment, FIG. 6 presents results for day 1 and day 5, while FIG. 9C compares day 1 to day 3.

Treatment with either DBZ (FIG. 9A, day 7) or DLL4 mAb (FIG. 6, day 5) resulted in a significant reduction ($p<0.01$) in tumor perfusion to 38.9±7.4% and 29.5±3.5%, respectively, relative to the vehicle group. We observed reduced tumor perfusion caused by DLL4 mAb treatment as early as 48 hr (FIG. 9C). When the contrast kinetics analysis was performed on day 3 for both the DBZ and DLL4 mAb experiments, the total contrast signal and the rate of contrast signal per second were decreased for both, as shown by the reduced slope and magnitude of the microbubble influx (FIG. 9B). Tumors treated with IR alone did not exhibit any significant alterations in tumor perfusion (compare IR groups in FIGS. 5, 9A, and 9C). Thus, global Notch inhibition or interruption of the DLL4-Notch axis profoundly disrupts tumor perfusion in both irradiated and unirradiated tumors.

CD31 Immunohistochemistry, Vessel Count, and Confocal Microscopy

Mice bearing LS174T xenograft in the DBZ experimental group and DLL4 mAb experimental group were sacrificed when tumor volume reached RTV4 and the tumors excised for immunohistochemistry (IHC) with anti-CD31 antibody. Microvascular counts were then performed on tumor sections. For the IHC, excised tumors were immediately placed in 4% paraformaldehyde overnight at 4° C., transferred to 25% glucose (in PBS) for an additional 24 hr 4° C., then snap frozen in isopentane cooled on dry ice, and stored in a –80° C. freezer until sectioned. For CD31 staining, rat anti-mouse CD31 (1:20 dilution, clone SZ31, Dianova) was used. Antigen retrieval was performed in target retrieval solution (S1700, Dako) using a Decloaking Chamber (Biocare Medical, CA). Sections were pretreated with 0.3% hydrogen peroxide in PBS for 20 min, followed by blocking buffer (see below) for 30 min and primary antibody in blocking buffer for 1 hr. Bound antibody was labeled with HRP conjugated rabbit anti-Rat IgG (1:100 dilution, Dako, UK) and visualized using 2,3-diaminobenzidine chromogen and counterstained with hematoxylin. Chalkley vessel counts were performed with a Chalkley point eyepiece graticule by two observers (S.K.L. and S.B.) on a minimum of three vessel 'hot spots' per tumor as previously described (Fox et al., Breast Cancer Res Treat. 1994, 29(1):109-16).

Figure 7A:
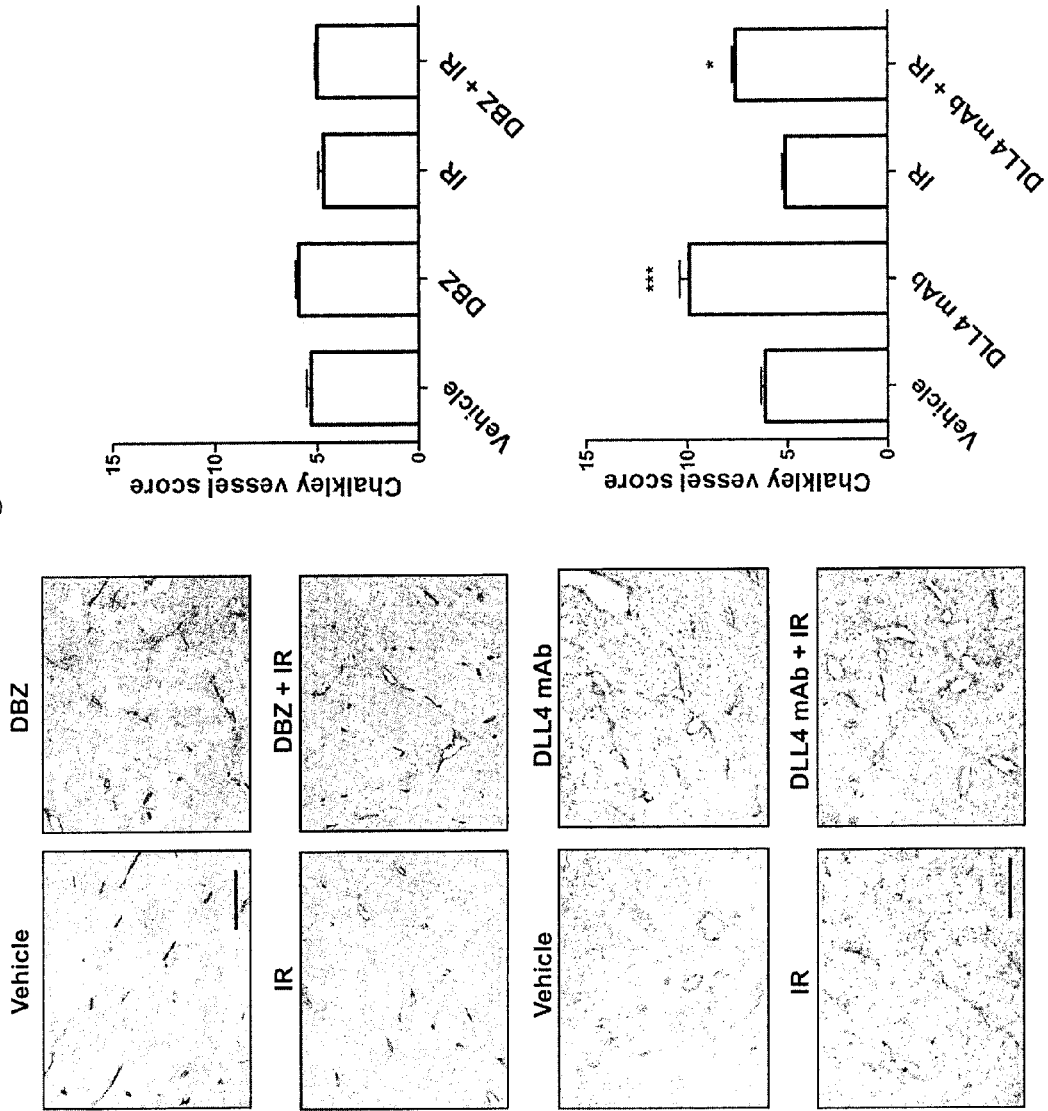
FIG. 7A presents IHC staining with anti-CD31 (left panels) and the Chalkley vessel counts in the bar graphs. *$p<0.05$, **$p<0.001$.

IHC using anti-CD31 antibody is shown in FIG. 7A, left panels, at 200×. Chalkley vessel counts were performed on a minimum of three tumors per group to quantify tumor microvasculature and the mean values and standard errors are shown in the bar graphs in FIG. 7A. There was a significant increase in vessel counts following treatment with DBZ ($p<0.05$), DLL4 mAb ($p<0.001$) and DLL4 mAb and IR ($p<0.05$). The vessel counts were increased substantially more with DLL4 mAb than DBZ (Chalkley vessel count 5.9±0.2 for DBZ treatment vs. 9.9±0.5 for DLL4 mAb treatment).

Figure 7B:
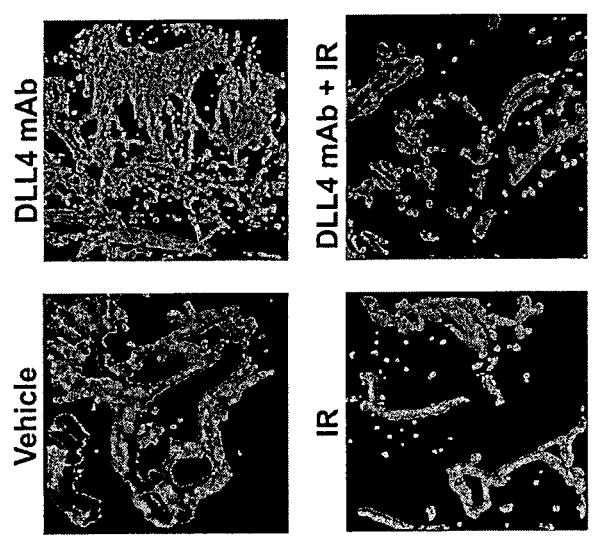
FIG. 7B shows 3D tumor vasculature reconstructions generated from confocal microscopy z-stack images of tumor sections obtained from mice following intravenous injection of anti-CD31-PE antibody.

For confocal microscopy and 3D reconstruction of the tumor vasculature, mice that had reached RTV4 from the DBZ experiment and from the DLL4 mAb experiment were injected with anti-CD31-phycoerythrin conjugated antibody (100 μL of 0.2 mg/mL; Biolegend) by lateral tail vein 4 min prior to sacrifice. For this analysis, tumors were immediately excised, and a central portion sectioned and immediately imaged using confocal microscropy (Leica). Confocal z-stacks of approximately 100 μm were taken at 0.5 μm intervals at 10× magnification, on multiple fields using the 543 nm laser to excite PE. Three-dimensional vascular reconstructions were constructed using Amira ResolveRT software (Visage Imaging). As shown in FIG. 7B, confocal microscopy and 3D reconstruction qualitatively revealed many more, smaller, highly branched and torturous vessels in tumors treated with DLL4 mAb compared to vehicle.

Tumor Hypoxia, Proliferation, and Necrosis

To detect hypoxia in the tumors, mice were injected i.p. with a mouse antibody to the hypoxic cell marker EF5 (clone: Elk3-51, kindly provided by Dr. C. Koch, University of Pennsylvania) that was directly conjugated to Cy3 fluorophore (10 μL/gm of 10 mM dissolved in 0.9% saline). Mice were sacrificed 2.5 hr later and tumors excised. For IHC, antigen retrieval was performed as described for anti-CD31 staining. Sections were pretreated with blocking buffer for 30 mins followed by the primary antibody for 24 hr at 4° C. Stained sections were mounted in aqueous mounting media containing 4',6-diamidino-2-phenylindole (DAPI). Stained tumour sections were observed field by field simultaneously by two independent observers (S.K.L. and S.B.) at 150× magnification. Each field was assigned a class score between 0 to 4 based on the percentage of the tumor area positive for EF5 staining (0, 0%; 1, >0% to 5%; 2, >5% to 15%; 3, >15% to 30%; 4, >30%); the score for each field was agreed upon by consensus. Areas of necrosis (see below) were identified using DAPI staining and were not included when estimating hypoxia scores. Scores obtained for each field were converted to percentages by using the median values for the corresponding group intervals. The mean for all scored fields was calculated for each tumor.

Figure 7C:
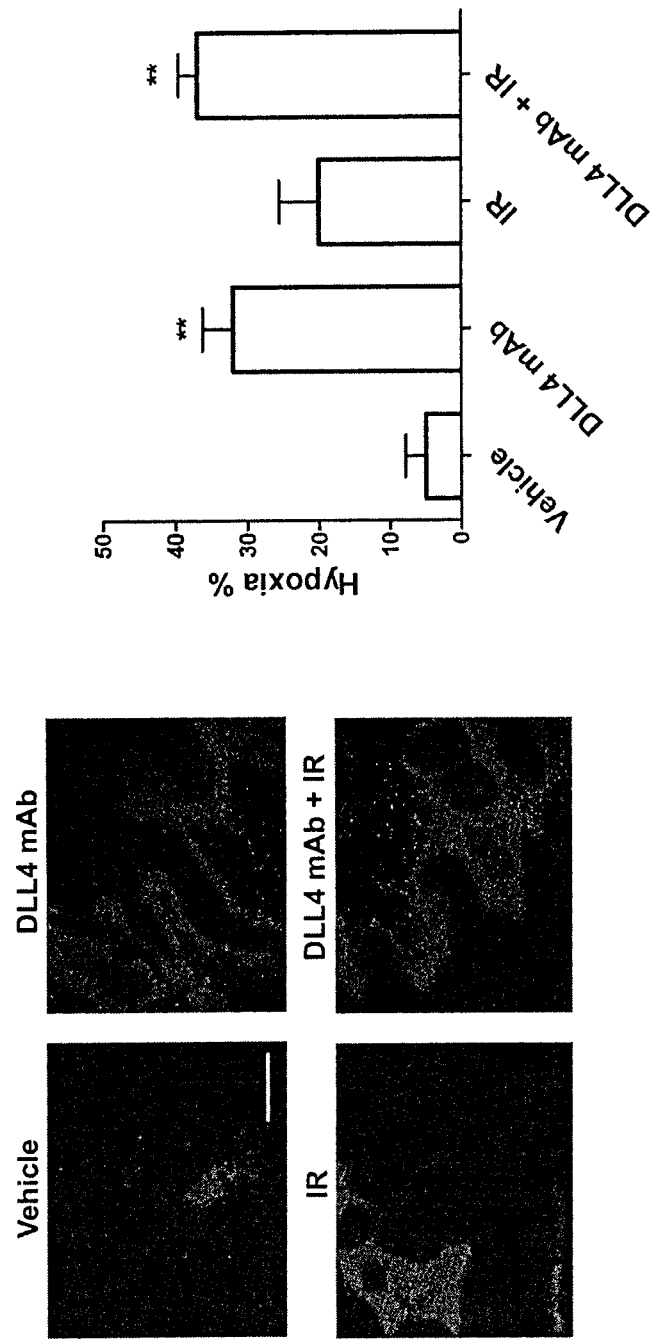
FIG. 7C presents EF5 IHC staining and the calculated mean hypoxic area. The left panel shows staining for the hypoxic marker EF5 in tumor sections from the indicated groups at 150×. Scale bar indicates 200 μm. The accompanying bar graph presents the mean hypoxia area of each tumor calculated as the average score for all of the fields for a minimum of three tumors per group. "**" denotes $p<0.001$ compared to vehicle.

The results are presented in FIG. 7C. The left panels show IHC staining for the hypoxic marker, EF5, in tumor sections at 150×. Whole sections were scored on a field-by-field basis to estimate the area of EF5 immunostained tumor cells and the mean hypoxia area of each tumor was calculated as the average score for all of the fields. Bar graphs presenting the percent hypoxia for vehicle, DLL4 mAb, IR, and DLL4 mAb with IR are shown in the right panel. Asterisk denotes significant difference from vehicle (**$p<0.001$). A minimum of three tumors were examined per group. A significant increase in hypoxia was observed for DLL4 mAb treatment, whether given alone or in combination with IR, consistent with non-functional angiogenesis and decreased perfusion. No significant increase in hypoxia was noted with DBZ (data not shown).

Cellular proliferation within the tumors was examined using Ki-67 staining. Mouse anti-human Ki-67 (1:100, clone 2531, ABO Serotec) was used. Antigen retrieval was performed using 10 mM sodium citrate, 0.05% TWEEN™ 20 (polysorbate 20), pH 6.0 at 90° C. for 20 min. Sections were pretreated with 0.3% hydrogen peroxide in PBS for 20 min. Endogenous biotin was blocked using Avidin/Biotin Blocking Kit (Vector) according to manufacturer's instructions followed by incubation with M.O.M™ blocking reagent (Vector Laboratories Ltd.) for 1 hr. Sections were incubated with blocking buffer for 5 min followed by the primary antibody in blocking buffer for 30 min. Bound antibody was labeled with biotinylated goat anti-mouse IgG antibody (1:500, Vector Laboratories Ltd.) followed by VECTASTAIN™ ABC Elite reagent, visualized using 2,3-diaminobenzidine chromogen and counterstained with hematoxylin. For Ki-67 scoring, the number of positive nuclei as a proportion of total nuclei was determined under a high power microscopic field (400×), and performed for a total of 6 random fields. Scoring was performed in viable tumor areas, avoiding regions of necrosis.

Figure 7D:
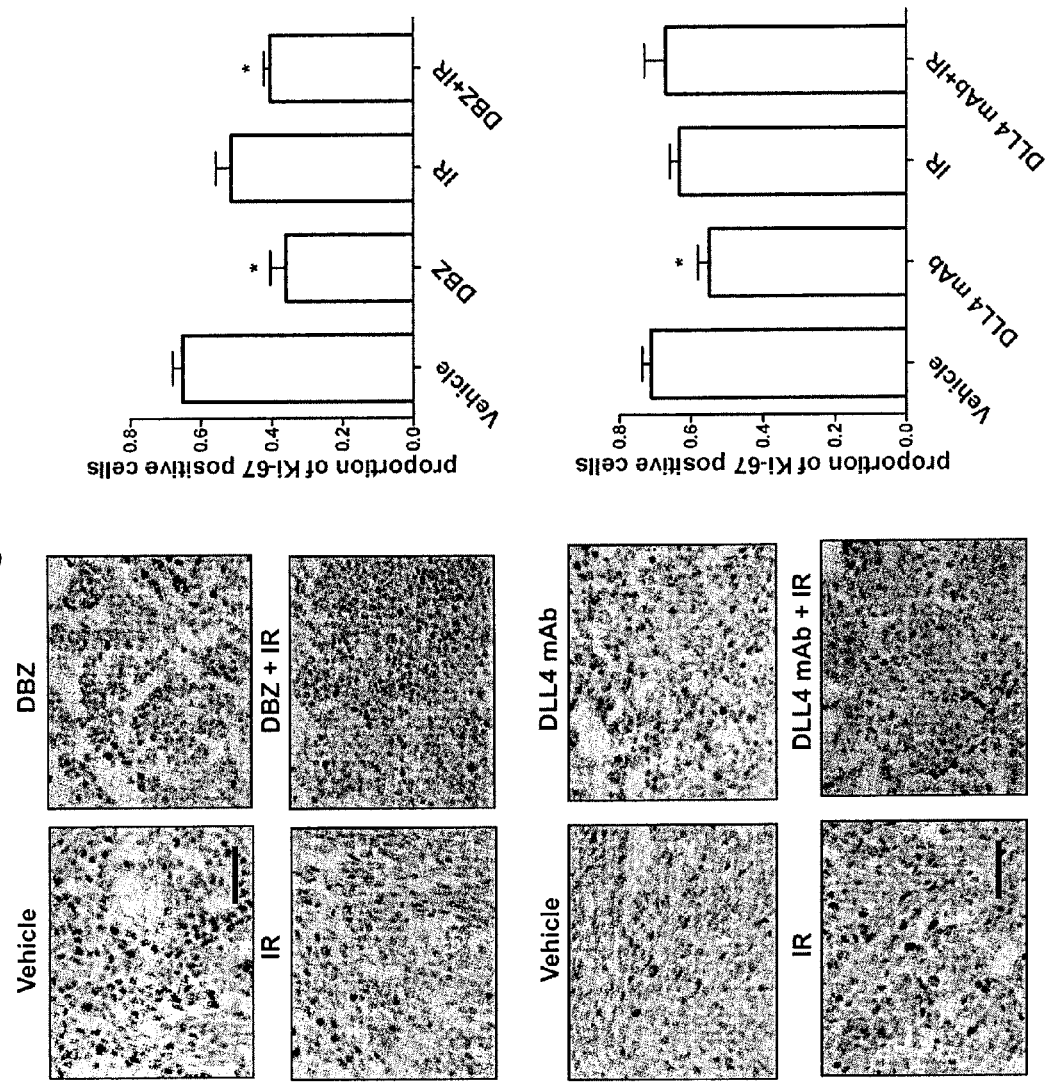
FIG. 7D presents Ki-67 IHC staining and the calculated proportion of Ki-67 positive cells. The left panel shows Ki-67 staining of tumor sections from the indicated groups at 400×. Scale bar indicates 50 μm. The accompanying bar graphs present the proportion of Ki-67 positive cells with standard error as determined from six high power fields using a minimum of three tumors per group. "**" denotes $p<0.01$ relative to vehicle.

Representative Ki-67 IHC images at 400× are shown in the left panels of FIG. 7D. Proliferating cells are identified by the brown (dark) colored nuclei. The proportion of Ki-67 positive cells to total number of cells was determined from six high power fields, and the mean values and standard errors plotted. The proportion of Ki-67 positive cells in each group from the DBZ experiment and the DLL4 mAb experiment is presented in the bar graphs. Asterisk denotes a statistically significant change relative to vehicle ("**" denotes $p<0.01$). A minimum of three tumors were examined per group. There was significantly decreased proliferation in the tumors obtained from mice treated with DBZ with or without IR, as well as in tumors from mice treated with DLL4 mAb alone.

Figure 7E:
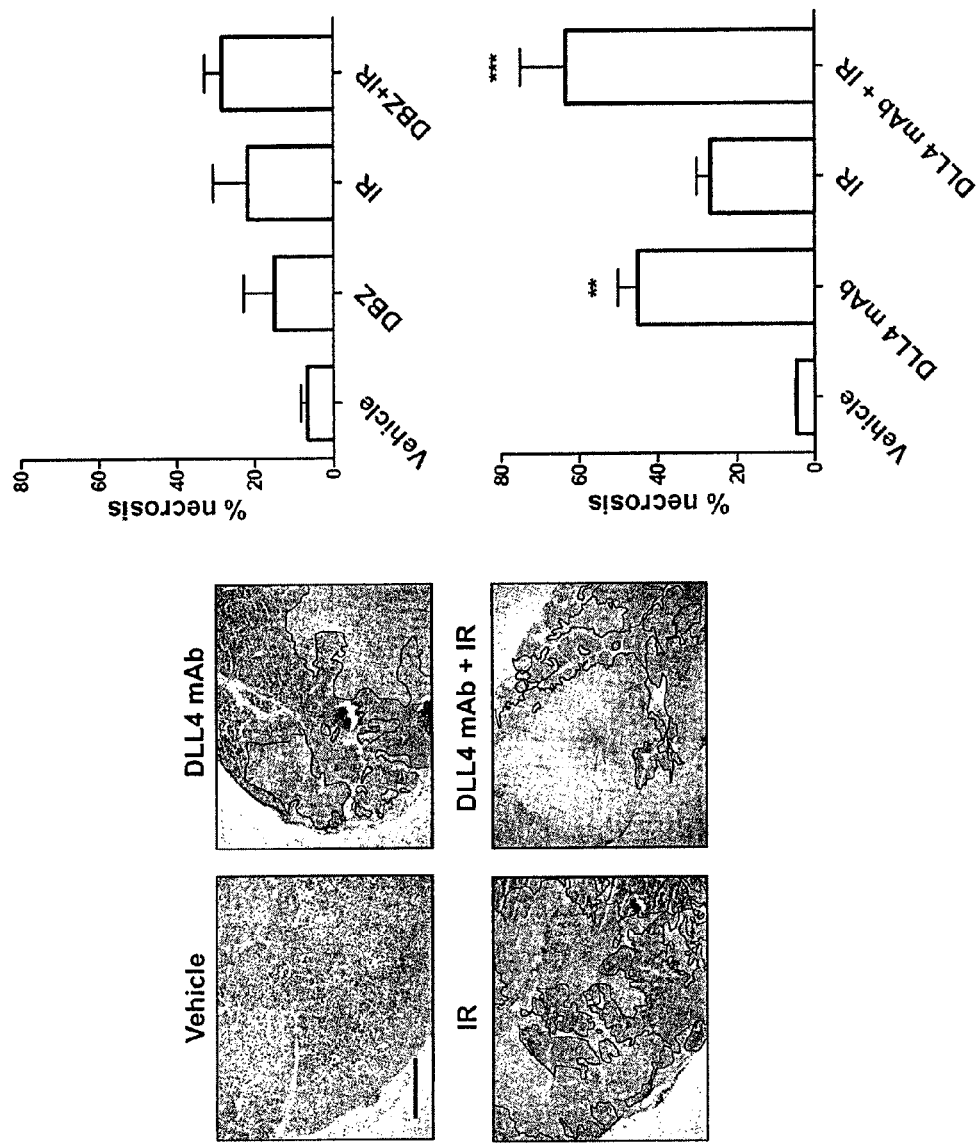
FIG. 7E presents H&E staining and the calculated percentage necrosis for tumors from the indicated groups. The H&E images in the left panels are shown at 20×. Scale bar indicates 1000 μm. Regions of necrosis are outlined in black. The accompanying bar graphs show the percentage of tumor necrosis estimated at low power for a minimum of three tumors per group, with standard error. $p<0.01$ and *$p<0.001$ relative to vehicle.

Levels of necrosis in the tumors was examined in conjunction with the EF5 IHC using the DAPI staining. Hematoxylin and eosin staining was also performed on tumor sections, and the estimated percentage of tumor necrosis under low power magnification was agreed upon by consensus from two independent investigators (S.K.L. and S.B.). Representative H&E staining images are shown at 20× in the left panels of FIG. 7E. Regions of necrosis are outlined in black. The percentage of tumor necrosis was estimated from the tumor at low power, the mean values and standard errors plotted, and the results presented in the bar graphs of FIG. 7E.

There was a trend towards increased tumor necrosis with DBZ (6.7±1.6%), and IR (15±7.6%), which was highest with combination treatment (28.3±4.4%), in comparison to vehicle (6.7±1.7%). DLL4 mAb treatment led to a significant and marked increase in tumor necrosis (45±5.0%) in comparison to vehicle-treated tumors (5.0±0.3%). That increase was further augmented when DLL4 mAb was used in combination with IR (63.3±11.7%). IR did not significantly increase tumor necrosis (26.7±3.3%). The tumor necrosis seen with combination IR and DLL4 mAb treatment was predominantly centrally located, reminiscent of histological findings characteristically seen with vascular disrupting agents. Thus, although the proportion of Ki-67 positive cells was not significantly different for DLL4 mAb and IR combination treatment compared to vehicle or IR, the overall amount of remaining viable tumor was considerably less, explaining the observed tumor growth delay.

DLL4 mAb treatment increased microvessel counts and tumor hypoxia

Figure 10B:
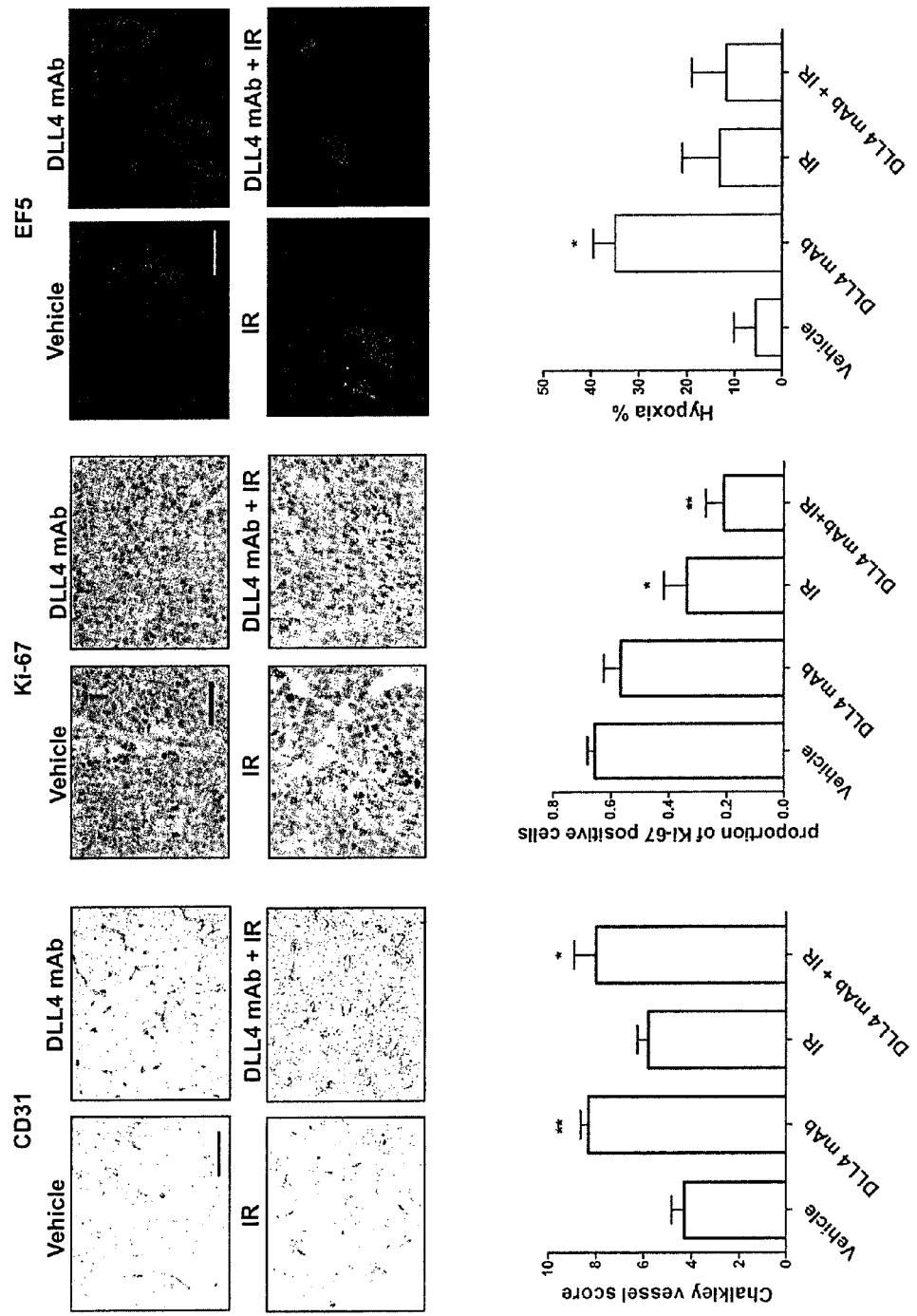
FIG. 10B presents immunohistochemistry staining of tumors from the perfusion study with anti-CD31, anti-Ki-67, and anti-EF5 antibodies and the resulting Chalkley vessel counts, proportion of Ki-67 positive cells, and hypoxic regions. "*" denotes p<0.05, and "**" denotes p<0.01 relative to vehicle.

To directly correlate the tumor perfusion changes observed following DLL4 mAb treatment with IHC, we sacrificed mice from the DLL4 mAb experiment following contrast ultrasound on day 5, and examined tumor vascular counts, hypoxia and proliferation. The results for this comparison are presented in FIG. 10B. Representative IHC images are shown as indicated (anti-CD31: 200×, scale bar indicates 100 µm; anti-Ki-67: 400×, scale bar indicates 50 µm; anti-EF5: 150×, scale bar indicates 200 µm). The bottom left panel in FIG. 10B presents bar graphs of Chalkley vessel counts. The middle bottom bar graph shows the proportion of Ki-67 positive cells. The percentage hypoxic regions are displayed in the bar graph to the right.

DLL4 mAb treatment significantly increased microvessel counts ($p<0.05$), reduced tumor perfusion, and increased hypoxia ($p<0.05$) relative to vehicle. Interestingly, this did not translate to significantly decreased tumor proliferation at this time point. In comparison, DLL4 mAb and IR combination treatment resulted in a trend towards increased microvessel counts, and a significant reduction in proliferation ($p<0.05$), but tumor hypoxia was not increased. This may be partly due to decreased oxygen consumption resulting from the lower tumor proliferation and hence, smaller tumor burden (i.e., note the lower mean tumor volume at day 5 with DLL4 mAb and IR treatment, compared to DLL4 mAb alone, in FIG. 5). The increase in tumor necrosis with combination treatment was not significant at this early time point (data not shown), suggesting that prolonged DLL4 blockade (>5 days) is required to induce necrosis.

Apoptosis is not a Major Route for Cell Death Following Notch Blockade or IR

To examine the role of apoptosis in cell death following Notch blockade, TUNEL staining was performed using APO-PTAG™ Peroxidase In Situ Apoptosis detection kit (Millipore). Sections were subjected to antigen retrieval using 10 mM Sodium Citrate, 0.05% TWEEN™ 20 (polysorbate 20), ph 6.0 at 90° C. for 20 min. The remainder of the procedure was performed according to manufacturer's instructions. Positive cells were visualized using 2,3-diaminobenzidine chromogen and counterstained with hematoxylin. TUNEL scoring was performed in the same manner as Ki-67 scoring, utilizing 6 random fields per tumor, and avoiding regions of necrosis.

Representative images at 400× are shown from tumor sections processed for TUNEL staining in FIG. 10A. On average, there were less than 1% TUNEL-positive cells seen per field for vehicle or treated tumor sections; scale bar indicates 50 µm. No significant difference in TUNEL-positive cells was noted as a result of any of the treatments, in agreement with the in vitro findings. This suggests that an increase in apoptosis was not responsible for the observed tumor growth delays, and that other mechanisms such as mitotic catastrophe may be a predominant mode of cell death.

To directly correlate the tumor perfusion changes with IHC, mice were sacrificed mice following contrast ultrasound on day 5, and tumor vascular counts, hypoxia, and proliferation examined (FIG. 10B). DLL4 mAb treatment significantly increased microvessel counts ($p<0.05$), reduced tumor perfusion, and increased hypoxia ($p<0.05$) relative to vehicle. Interestingly, this did not translate to significantly decreased tumor proliferation at this time point. In comparison, DLL4 mAb and IR combination treatment resulted in a trend towards increased microvessel counts, and a significant reduction in proliferation ($p<0.05$), but tumor hypoxia was not increased. This may be partly due to decreased oxygen consumption resulting from the lower tumor proliferation and hence, smaller tumor burden (i.e., note the lower mean tumor volume at day 5 with DLL4 mAb and IR treatment, compared to DLL4 mAb alone, in FIG. 5). We did not note a significant increase in tumor necrosis with combination treatment (data not shown) at this early time point, suggesting that prolonged DLL4 blockade (>5 days) is required to induce necrosis.

IHC staining for DLL4 in tumor sections revealed increased DLL4 expression following Notch inhibition with DBZ or DLL4 mAb consistent with our in vitro data (data not shown).

Example 6

DLL4 Blockade Synergizes with IR to Delay Tumor Growth Independent of Tumor DLL4

IHC staining for DLL4 in tumor sections revealed increased DLL4 expression following Notch inhibition with DBZ or DLL4 mAb consistent with our in vitro data (data not shown). For DLL4 staining, the anti-DLL4 monoclonal antibody clone 242 (generated in VELOCIMMUNE™ mice (Regeneron Pharmaceuticals Inc., USA)) was used. The variable regions of this antibody are fully human and the Fc-domain is mouse. Clone 242 binds to an epitope in EGF-like domains 3-5 of the extracellular domain of human DLL4. Antigen retrieval was performed in target retrieval solution (S1700, Dako) using a DECLOAKING CHAMBER™ (Biocare Medical, USA). Sections were pretreated with 0.3% hydrogen peroxide in PBS for 20 min and M.O.M™ blocking reagent (Vector Laboratories Ltd.) for 1 hr. Sections were incubated for 5 min with blocking buffer (0.1 M Tris-HCl, pH 7.5, 150 mM NaCl, 0.5% TSA™ Blocking Reagent (Perkin Elmer)) followed by the primary antibody at 1 µg/ml in blocking buffer for 30 min. Bound antibody was labeled and visualized using ENVISION™+HRP Mouse kit (Dako) according to the manufacturer's instructions and counterstained with hematoxylin.

To determine whether tumor DLL4 was a significant target, we tested the effect of DLL4 mAb on xenografts from FaDu cells that do not express DLL4 (FIG. 8A). Although DLL4 expression was undetectable by western blotting of FaDu cells; in comparison, LS174T lysates had abundant expression of DLL4. Equal loading was confirmed with β-actin. Western blotting of untreated human FaDu carcinoma cells confirmed expression of Notch 1-4 receptors, and Jagged-1 (FIG. 8A).

FaDu tumors were grown in Nude mice treated with vehicle, DLL4 mAb, a 5 Gy dose of IR, or DLL4 mAb with IR. Details regarding the xenografting are presented in previous experiments, but briefly 5×10$^6$ FaDu cells were mixed with Matrigel in a 1:1 ratio, and injected subcutaneously into the right flank of six to seven week old female BALB/C nude mice. Tumor volume was determined by the modified ellipse formula (volume=length×width$^2$÷2). When the xenograft tumors reached approximately 100 mm$^3$ volume, the mice were randomized into vehicle or experimental arms.

Figure 8B:
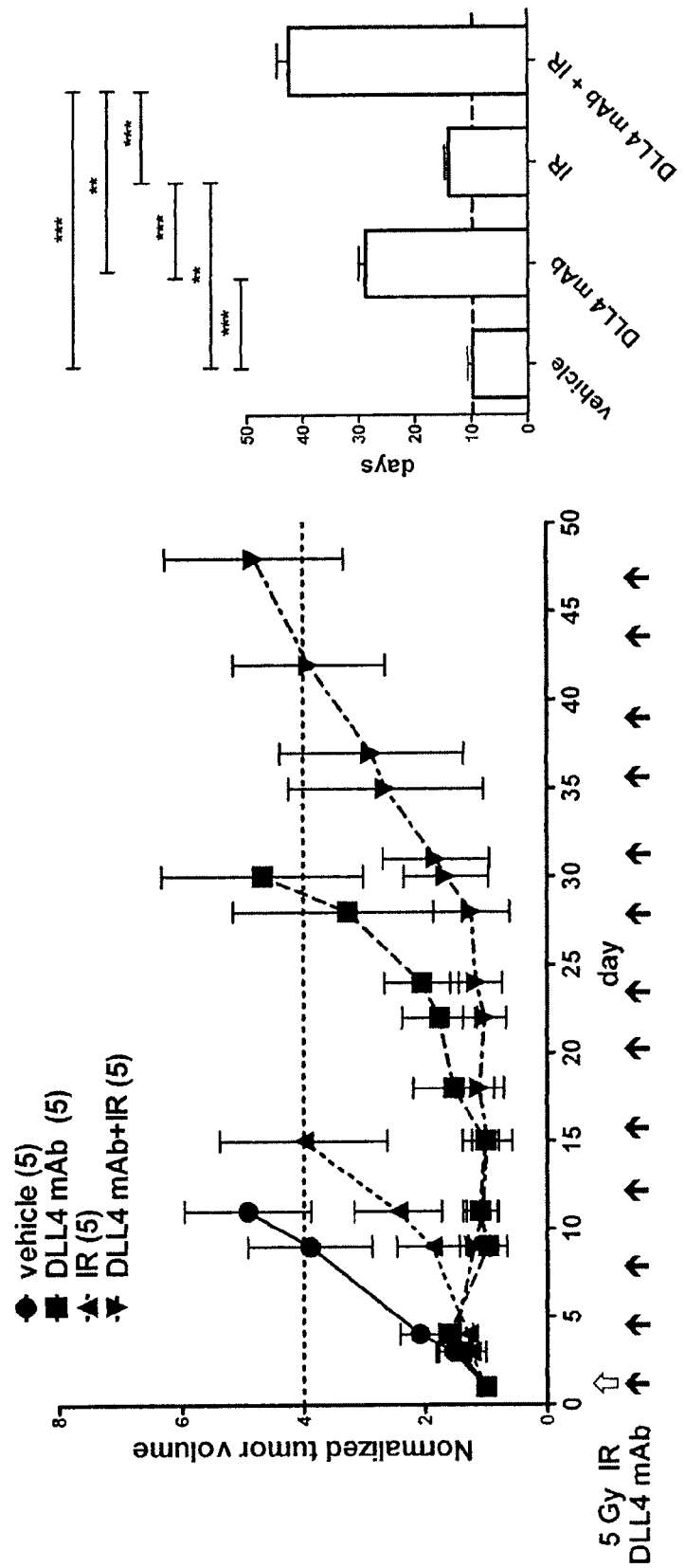
FIG. 8B depicts the effect of therapy on FaDu tumor volume. The survival graph shows the treatment course, as indicated by the arrow heads on the X-axis, versus the normalized tumor volume on the Y-axis for vehicle (circle, N=), DLL4 mAb (square, N=5), 5 Gy IR (triangle, N=5), and 5 Gy IR plus DLL4 mAb (inverted triangle, N=5). The bar graph on the right depicts the average time for tumors to reach four times the starting volume (RTV4) along with standard deviations. The dotted line indicates RTV4 for the vehicle-treated tumors; the extent of the respective bars above this line corresponds to tumor growth delay. "*" denotes $p<0.001$, and "" denotes $p<0.01$ relative to vehicle.

DLL4 mAb was given twice per week for the duration of the experiment, as depicted by arrowheads in the survival graph shown in FIG. 8B. The tumor volumes were normalized relative to day 1 tumor volumes, and the mean normalized tumor volumes and standard deviation plotted on the survival curve. Mice were sacrificed when their normalized tumor volumes reached RTV4, shown as a dotted line on the survival curve. The total number of mice in each group is shown in the legend within parentheses. The bar graph on the right in FIG. 8B shows the average time for tumors to reach RTV4, along with standard deviations. The dotted line indicates RTV4 for the vehicle-treated tumors. Thus, the extent of the respective bars above this line corresponds to tumor growth delay.

The numerical results are presented in Table 3.

TABLE 3

| Group | FaDu RTV4 (days) | Tumor Growth Delay (days) |
|---|---|---|
| Vehicle | 9.8 ± 2.2 | |
| DLL4 mAb | 28.8 ± 2.6 | 19.0 ± 3.4 |
| IR | 14.0 ± 1.6 | 4.2 ± 2.7 |
| DLL4 mAb + IR | 42.6 ± 4.5 | 32.8 ± 5.0 |

The average RTV4 for the vehicle-treated group was 9.8±2.2 days, and for mice treated with IR, it was 14.0±1.6 days, yielding a tumor growth delay for IR of 4.2±2.7 days. The RTV4 for DLL4 mAb was 28.8±2.6 days, resulting in a profound tumor growth delay of 19.0±3.4 days. Combination therapy of DLL4 mAb and IR yielded a RTV4 of 42.6±4.5 days, corresponding to a synergistic tumor growth delay of 32.8±5.0 days.

DISCUSSION

DLL4-Notch blockade promoted non-productive tumor angiogenesis (increase in vessel density, and paradoxical decrease in tumor perfusion) and resulted in tumor growth delay; however, a significant, synergistic enhancement of tumor growth delay occurred when it was combined with IR due to extensive tumor necrosis. Additionally, there was effective growth delay with anti-DLL4 blocking antibody, and synergy with IR when a human hypopharyngeal squamous cell carcinoma xenograft that lacks endogenous DLL4 was tested, demonstrating the important contribution of DLL4-Notch signaling for maintaining tumor growth and survival, independent of tumor DLL4 expression. Together, the data highlight the importance of disrupting DLL4-Notch signaling for delaying tumor growth, and the broad relevance for this treatment approach in different tumor types, independent of tumor DLL4 expression. Thus, combining DLL4-Notch blockade with IR to promote non-functional tumor angiogenesis and necrosis will be broadly applicable to solid tumors, and provides support for testing in an early phase clinical trial.

In clinical radiotherapy, single dose IR is not commonly given at a dose high enough to cause ablation of tumor angiogenesis, with the exception being stereotactic radiosurgery; thus targeting tumor angiogenesis will be a useful strategy in the majority of clinical situations. The 5 Gy dose of IR used in the initial animal studies is well within a dose range that is commonly used clinically. For example, single doses of irradiation in the range of 8 Gy are often used for treatment of malignant spinal cord compression, bone metastases, or bulky compressive lesions. Thus, symptoms and tumor control could be improved by administering Notch inhibitors after those standard irradiation therapies. In other cases, it will be appropriate to combine a Notch inhibitor with a fractionated radiotherapy schedule and/or to use a different sequencing for the inhibitor and IR.

There is evidence that Notch signaling initiated between endothelial and tumor cells can alter the tumor microenvironment. Expression of the Notch ligands, DLL4 or Jagged-1, on tumor cells can trigger Notch signaling on adjacent endothelial cells, altering tumor angiogenesis and enhancing tumor growth (Li et al., Cancer Cell 2005, 8(1):1-3; Li & Harris, Front Biosci. 2009, 14:3094-110; Zeng et al. Cancer Cell 2005, 8(1):13-23). Likewise, stromal cells can induce Notch signaling in tumor cells, which has been implicated in tumor escape from dormancy (Indraccolo et al. Cancer Res. 2009, 69(4):1314-23), as well as tumor intravasation and metastasis (Sonoshita et al. Cancer Cell 2011, 19(1):125-137). Calabrese et al. reported that a perivascular niche is important for maintaining brain tumor stem cells, and that disruption of this niche with anti-angiogenics, impairs tumor growth (Calabrese et al. Cancer Cell 2007, 11(1):69-82). As well, tumor explants from glioblastoma multiforme (GBM) patients grown in a transwell system, showed decreased tumor cell proliferation and self-renewal after treatment with a GSI, and this potentiated the effects of radiation; this was postulated to occur due to an anti-angiogenic effect of Notch blockade with disruption of the vascular niche (Hoving a et at Stem Cells 2010, 28(6):1019-29). However, a limitation of an explant model is that important contributors and properties of the tumor microvasculature such as infiltrating bone marrow derived cells, or cyclical tumor hypoxia cannot be accounted for, unlike an in vivo xenograft system. Indeed, there was no improvement of radioresponse of tumor cells by DBZ or DLL4 mAb in vitro; instead, significant tumor growth delay was only seen in vivo. Future work will be directed at using in vivo markers for CSCs and Notch activity to explore the influence of Notch inhibitors and IR on CSC fate within the context of these tumor types. Interestingly, a role of GBM CSC differentiation into tumor vasculature has been recently demonstrated by two groups (Ricci-Vitiani et al. Nature 2010, 468(7325):824-28; Wang et al. Nature 2010, 468(7325):829-33), and differentiation to endothelial progenitors was blocked by a γ-secretase inhibitor (Wang et al. Nature 2010, 468(7325):829-33).

DLL4 mAb is considerably more effective than DBZ in delaying tumor growth, either as sole treatment, or in combination with IR. DBZ has been reported to have low plasma levels due to poor i.p. absorption and/or rapid elimination (<12 hr) (Milano et al., Toxicol Sci. 2004, 82(1):341-58). Thus, the longer plasma half-life of a monoclonal antibody would be expected to provide continuous, effective blockade of DLL4-Notch signaling, whereas Notch inhibition resulting from DBZ would be expected to wane between dosing intervals. Additionally, an increase in tumor DLL4 expression followed Notch blockade both in vitro and in vivo, and the resulting increased levels of DLL4 on the tumor surface could theoretically be blocked from signaling more effectively with DLL4 mAb. Another translational advantage of utilizing DLL4 mAb over a GSI, is that it avoids dose-limiting gastrointestinal toxicity caused by conversion of proliferative crypt cells into goblet cells (Milano et al., Toxicol Sci. 2004, 82(1):341-58; van Es et al., Nature 2005, 435(7044):959-63); although there wasn't any significant toxicity of DBZ as measured by weight loss in the current study (data not shown), DBZ was only administered every third day for a maximum of five doses as this has previously been shown to be a safe schedule (J. L. Li, unpublished data). If more frequent and prolonged dosing had been possible, this may have resulted in improved tumor growth delay with DBZ. Attempts have been made to reduce GI toxicity resulting from GSI treatment, such as through concurrent administration of glucocorticoids (Real & Ferrando, Leukemia 2009, 23(8):1374-7).

The development of monoclonal blocking antibodies specific for Notch1 or Notch2 receptors, has successfully avoided the dose-limiting GI toxicity (goblet cell metaplasia appears to require both Notch1 and Notch2 blockade), while retaining potent anti-tumor activity (Wu et al., Nature 2010; 464(7291):1052-7). Thus, future experiments examining additional specific Notch pathway inhibitors, including blocking mAbs against Notch1 or Notch2, or Notch ligands, Jagged-1 or DLL1, in combination with IR in these preclinical models will be of importance; this may well be needed if redundancy in Notch signaling within the tumor microenvironment is demonstrated. Notably, the xenografts experiments herein expressed Jagged-1, and a priori a more comprehensive inhibition of Notch signaling via DBZ treatment was expected to be more effective in delaying tumor growth. However, the antibody was far more effective in the current experiments. It is surprising that Jagged-1 expression on the tumors did not activate Notch in the absence of DLL4, but it may be that the accumulated DLL4 could compete with Jagged-1 as was seen in an angiogenesis retinal model (Benedito et al., Cell 2009, 137(6):1124-35). Lee et al., explored combination anti-VEGF mAb with IR (20-40 Gy) for normoxic or hypoxic LS174T xenograft tumors, and the effect on tumor growth delay was additive at best; the exception was seen only with the highest dose of IR (40 Gy) and hypoxic tumors (Lee et al., Cancer Res. 2000, 60(19):5565-70). In comparison, using the same xenograft system, synergistic tumor growth delay was obtained following DLL4 blockade and IR, and this occurred at a lower, more clinically relevant IR dose. Given the previously reported findings that DLL4 blockade is able to overcome tumors resistance to anti-VEGF therapy in preclinical models (Ridgway et al. Nature 2006, 444(7122):1083-7; Li et al., Cancer Res 2007, 67(23):11244-53), it will be interesting to explore this approach of combination Notch inhibition and VEGF inhibition with radiotherapy.

The current study is the first report of in vivo findings for a DLL4 inhibitor combined with IR therapy in tumor xenograft models. That combination prolonged tumor growth delay, and is clinically relevant. In conclusion, the use of DLL4 inhibitors following IR to generate non-productive angiogenesis and profound tumor necrosis is an effective approach to reduce tumor growth or recurrence.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating cancer cells expressing Delta-like ligand 4 (DLL4) in a human comprising administering a therapeutically effective amount of ionizing radiation and an anti-DLL4 antibody or a DLL4-binding fragment thereof,
    wherein the anti-DLL4 antibody or DLL4-binding fragment antagonizes the biological activity of DLL4, and
    wherein the anti-DLL4 antibody or anti-DLL4-binding fragment thereof comprises:
        a heavy chain variable domain as set forth in SEQ ID NO: 7; and
        a light chain variable domain as set forth in SEQ ID NO: 8.

2. A method of reducing or inhibiting tumor cell proliferation or tumor angiogenesis in tumor cells expressing Delta-like ligand 4 (DLL4) in a human comprising administering a therapeutically effective amount of ionizing radiation and an anti-DLL4 antibody or a DLL4-binding fragment thereof,
    wherein the anti-DLL4 antibody or the DLL4-binding fragment antagonizes the biological activity of DLL4, and
    wherein the anti-DLL4 antibody or anti-DLL4-binding fragment thereof comprises:
        a heavy chain variable domain as set forth in SEQ ID NO: 7; and a light chain variable domain as set forth in SEQ ID NO: 8.

3. A method of reducing invasion or metastasis of malignant tumor cells expressing Delta-like ligand 4 (DLL4) in a human comprising administering a therapeutically effective amount of ionizing radiation and an anti-DLL4 antibody or a DLL4-binding fragment thereof,
wherein the anti-DLL4 antibody or the DLL4-binding fragment antagonizes the biological activity of DLL4, and
wherein the anti-DLL4 antibody or anti-DLL4-binding fragment thereof comprises:
a heavy chain variable domain as set forth in SEQ ID NO: 7; and
a light chain variable domain as set forth in SEQ ID NO: 8.

4. A method of reducing or inhibiting a neoplasia comprising neoplastic cells expressing Delta-like ligand 4 (DLL4) in a human comprising administering a therapeutically effective amount of ionizing radiation and an anti-DLL4 antibody or a DLL4-binding fragment thereof,
wherein the anti-DLL4 antibody or the DLL4-binding fragment antagonizes the biological activity of DLL4, and
wherein the anti-DLL4 antibody or anti-DLL4-binding fragment thereof comprises:
a heavy chain variable domain as set forth in SEQ ID NO: 7; and
a light chain variable domain as set forth in SEQ ID NO: 8.

5. A method of delaying tumor regrowth of a tumor comprising cells expressing Delta-like ligand 4 (DLL4) in a subject following treatment with at least one dose of ionizing radiation comprising administering to the subject a therapeutically effective amount of an anti-DLL4 antibody or a DLL4-binding fragment thereof,
wherein the anti-DLL4 antibody or the DLL4-binding fragment antagonizes the biological activity of DLL4, and
wherein the anti-DLL4 antibody or anti-DLL4-binding fragment thereof comprises:
a heavy chain variable domain as set forth in SEQ ID NO: 7; and
a light chain variable domain as set forth in SEQ ID NO: 8.

6. The method of any one of claims 1 to 5, wherein the cancer, tumor, or neoplasia is colorectal cancer, metastatic colon cancer, colon cancer, rectal cancer, glioblastoma, breast cancer, non-small cell lung cancer, head and neck cancer, renal cell carcinoma, cervical cancer, ovarian cancer, or prostate cancer.

7. The method of claim 1, wherein the anti-DLL4 antibody or the DLL4-binding fragment thereof is human.

8. The method of claim 1, wherein the dose of the anti-DLL4 antibody or DLL4-binding fragment thereof is about 0.1 to about 10 milligrams/kilogram (mg/kg).

9. The method of claim 8, wherein the anti-DLL4 antibody or DLL4-binding fragment thereof is administered twice per week.

10. The method of claim 1, wherein the anti-DLL4 antibody or DLL4-binding fragment thereof is administered following the first dose of ionizing radiation administered.

11. The method of claim 1, wherein the anti-DLL4 antibody or DLL4-binding fragment thereof is administered before the first dose of ionizing radiation is administered.

12. The method of claim 1, wherein the anti-DLL4 antibody or DLL4-binding fragment thereof is administered on the same day as the first dose of ionizing radiation is administered.

13. The method of claim 1, wherein the total dose of ionizing radiation is about 45 grays (Gy) to about 80 Gy.

14. The method of claim 13, wherein the ionizing radiation is administered in fractionated doses of from about 1.5 to about 3.5 Gy/day.

15. The method claim 1, wherein the ionizing radiation is palliative and the total dose of ionizing radiation is about 8 Gy to about 60 Gy.

16. The method of claim 15, wherein the ionizing radiation is administered in fractionated doses of from about 3 to about 8 Gy/day.

17. The method claim 1, wherein the method further comprises administering a chemotherapeutic drug.

* * * * *

UNITED STATES PATENT AND TRADEMARK OFFICE
CERTIFICATE OF CORRECTION

PATENT NO. : 8,685,401 B2  
APPLICATION NO. : 13/524396  
DATED : April 1, 2014  
INVENTOR(S) : Adrian Harris et al.

Page 1 of 1

It is certified that error appears in the above-identified patent and that said Letters Patent is hereby corrected as shown below:

Title Page, Item (60), "Provisional application No. 61/498,220" should read --Provisional application No. 61/498,200--.

Signed and Sealed this  
Second Day of September, 2014

Michelle K. Lee  
*Deputy Director of the United States Patent and Trademark Office*